(12) United States Patent
Yu et al.

(10) Patent No.: US 11,918,599 B2
(45) Date of Patent: Mar. 5, 2024

(54) COMPOSITION FOR PREVENTING OR TREATING NEUROINFLAMMATORY DISEASE COMPRISING DIDANOSINE

(71) Applicants: GliaCellTech Inc., Seoul (KR); Daegu Gyeongbuk Institute of Science and Technology, Daegu (KR)

(72) Inventors: Seong-Woon Yu, Daegu (KR); Hyeri Nam, Daegu (KR); Younghwan Lee, Seoul (KR)

(73) Assignees: Daegu Gyeongbuk Institute of Science and Technology, Daegu (KR); GliaCellTech Inc., Seoul (KR)

( * ) Notice: Subject to any disclaimer, the term of this patent is extended or adjusted under 35 U.S.C. 154(b) by 0 days.

(21) Appl. No.: 18/047,392

(22) Filed: Oct. 18, 2022

(65) Prior Publication Data
US 2023/0147946 A1 May 11, 2023

Related U.S. Application Data

(63) Continuation of application No. PCT/KR2021/017068, filed on Nov. 19, 2021.

(30) Foreign Application Priority Data

Nov. 19, 2020 (KR) ........................ 10-2020-0156060

(51) Int. Cl.
| | | |
|---|---|---|
| A01N 43/04 | (2006.01) |
| A61K 31/70 | (2006.01) |
| A61K 31/7068 | (2006.01) |
| A61P 25/28 | (2006.01) |
| A61P 29/00 | (2006.01) |

(52) U.S. Cl.
CPC ......... *A61K 31/7068* (2013.01); *A61P 25/28* (2018.01); *A61P 29/00* (2018.01)

(58) Field of Classification Search
None
See application file for complete search history.

(56) References Cited

U.S. PATENT DOCUMENTS

2018/0099939 A1    4/2018   Zhang et al.

FOREIGN PATENT DOCUMENTS

| KR | 10-2007-0026660 | 3/2007 |
| KR | 10-2007-0089926 | 9/2007 |
| KR | 10-2012-0118088 | 10/2012 |
| KR | 10-2014-0134170 | 11/2014 |
| KR | 10-2015-0119089 | 10/2015 |
| WO | WO-2019246422 A1 * | 12/2019 ............. A61K 31/13 |

OTHER PUBLICATIONS

KIPO, PCT Search Report & Written Opinion of PCT/KR2021/017068 dated Feb. 28, 2022.
Yu Zhu et al., "CXCR3 activation by lentivirus infection suppresses neuronal autophagy: neuroprotective effects of antiretroviral therapy", The FASEB Journal, 2009, pp. 2928-2941, doi: 10.1096/fj.08-128819.
Brian Giunta et al., "Antiretroviral medications disrupt microglial phagocytosis of b-amyloid and increase its production by neurons: Implications for HIV-associated neurocognitive disorders", Molecular Brain 2011, 4:23.
Sonja G Schütz et al., "HIV-related neuropathy: current perspectives", HIV/AIDS—Research and Palliative Care, 2013, pp. 243-251.
David V. Hansen et al., "Microglia in Alzheimer's disease", J. Cell Biol. vol. 217 No. 2 459-472, https://doi.org/10.1083/jcb.201709069.
Marius Krauthausen et al., "CXCR3 promotes plaque formation and behavioral deficits in an Alzheimer's disease model", The Journal of Clinical Investigation vol. 125 No. 1 Jan. 2015, pp. 365~378.
Haowei Jiang et al., "A Review of the Familial Alzheimer's Disease Locus PRESENILIN 2 and Its Relationship to PRESENILIN 1", Journal of Alzheimer's Disease 66 (2018) 1223-1339, DOI 10.3233/JAD-180656.
Mi-Hyang Cho et al., "Autophagy in microglia degrades extracellular B-amyloid fibrils and regulates the NLRP3 inflammasome", Autophagy 10, 1761-1775, Oct. 2014.
Sadim Jawhar et al., "Motor deficits, neuron loss, and reduced anxiety coinciding with axonal degeneration and intraneuronal Aβ aggregation in the 5XFAD mouse model of Alzheimer's disease", Neurobiology of Aging 196. e29-40 (2012).

* cited by examiner

*Primary Examiner* — Patrick T Lewis
(74) *Attorney, Agent, or Firm* — LEX IP MEISTER, PLLC

(57) ABSTRACT

The present invention relates to a composition for preventing or treating a neuroinflammatory disease, which can inhibit the expression of neuroinflammatory cytokines, promote the degradation of amyloid beta, and improve a cognitive function in an animal model of Alzheimer's disease. More specifically, the present invention relates to a composition for preventing or treating a neuroinflammatory disease comprising didanosine or a pharmaceutically acceptable salt thereof, and the composition may be used for the development of drugs and quasi-drug materials.

12 Claims, 19 Drawing Sheets
Specification includes a Sequence Listing.

COMPOSITION FOR PREVENTING OR TREATING NEUROINFLAMMATORY DISEASE COMPRISING DIDANOSINE

TECHNICAL FIELD

The present disclosure relates to a composition for preventing or treating neuroinflammatory disease and, more specifically, to a composition comprising didanosine or a pharmaceutically acceptable salt thereof for prevention or treatment of neuroinflammatory disease.

BACKGROUND ART

The central nervous system consists of neurons and glial cells. Glial cells account for about 90% of the total brain cells, and about 50% of the total brain volume. Glial cells can be further classified into the following three types: astrocytes, microglia, and oligodendrocytes. Among them, microglia are a type of differentiated (specialized) macrophages and are widely distributed in the brain. Microglia not only act as phagocytes that engulf tissue debris and dead cells, but also participate in the braids biodefense activities.

Neuroinflammation, a kind of immune response of the nervous system, has a close relationship with many neurodegenerative diseases comprising Alzheimer's disease, Parkinson's disease, and multiple sclerosis, and is currently considered a hallmark of neurodegenerative diseases. Neuroinflammatory responses include activation of innate immune cells (microglia), release of inflammatory mediators such as nitric oxide (NO), cytokines and chemokines, and macrophage infiltration, leading to neuronal cell death. Inflammatory activation of microglia and astrocytes is thought to be a pathological hallmark and an important mechanism in the progression of neurodegenerative diseases. Since strict regulation of microglial activity is essential for maintaining brain homeostasis and preventing infectious and inflammatory diseases, it is necessary to develop a substance that can modulate the activity of microglia to alleviate neuroinflammation.

Didanosine is an FDA-approved medication used in the treatment of HIV/AIDS. As a nucleoside reverse transcriptase inhibitor, didanosine inhibits HIV reverse transcriptase by competing with natural dATP, and acts as a chain terminator by its incorporation into viral DNA as the lack of a 3'-OH group in the incorporated nucleoside analogue prevents the formation of the 5' to 3' phosphodiester linkage essential for DNA chain elongation. With the ability to cross the blood-brain barrier, didanosine can easily affect the brain. However, the effect of using didanosine to suppress neuroinflammation or act on the brain is unknown, and thus there is a need for research on the effect.

DISCLOSURE

Technical Problem

To this end, an aspect of the present disclosure is to provide a composition comprising didanosine or a pharmaceutically acceptable salt thereof for prevention, alleviation, or treatment of neuroinflammatory disease.

Another aspect of the present disclosure is to a method for preventing or treating a neuroinflammatory disease, the method comprising a step of administering a composition comprising didanosine or a pharmaceutically acceptable salt thereof to a subject in need thereof.

A further aspect of the present disclosure is to provide a use of didanosine or a pharmaceutically acceptable salt thereof for preventing or treating a neuroinflammatory disease.

In an embodiment of the present disclosure, the composition may promote degradation of amyloid beta.

In another embodiment of the present disclosure, the composition may inhibit neuroinflammation and recover memory.

However, the technical purposes to be achieved by the present disclosure are not limited to the above-mentioned purposes, and other purposes not mentioned will be clearly understood by those skilled in the art from the following description.

Technical Solution

An aspect of the present disclosure pertains to a pharmaceutical composition for prevention or treatment of a neuroinflammatory disease, comprising didanosine or a pharmaceutically acceptable salt thereof.

Another aspect of the present disclosure pertains to a composition comprising didanosine or a pharmaceutically acceptable salt thereof for promoting amyloid beta degradation in microglia.

Another aspect of the present disclosure pertains to an anti-inflammatory composition against nervous system inflammation, the composition comprising didanosine or a pharmaceutically acceptable salt thereof.

Another aspect of the present disclosure pertains to a composition comprising didanosine or a pharmaceutically acceptable salt thereof for improving memory.

Another aspect of the present disclosure pertains to a method for prevention or treatment of a neuroinflammatory disease, the method comprising a step of administering a composition comprising didanosine or a pharmaceutically acceptable salt thereof to a subject.

Another aspect of the present disclosure pertains to a use of a composition comprising didanosine or a pharmaceutically acceptable salt thereof for preventing or treating a neuroinflammatory disease.

Another aspect of the present disclosure pertains to a use of didanosine or a pharmaceutically acceptable salt thereof for producing a pharmaceutical composition for prevention or treatment of a neuroinflammatory disease.

Another aspect of the present disclosure pertains to a pharmaceutical composition for use in preventing or treating a neuroinflammatory disease, comprising didanosine or a pharmaceutically acceptable salt thereof.

Below, a detailed description will be given of the present disclosure.

An aspect of the present disclosure is drawn to a pharmaceutical composition for prevention or treatment of neuroinflammatory disease, comprising didanosine or a pharmaceutically acceptable salt thereof.

As used herein, the term "didanosine" refers to the compound which has the empirical formula $C_{10}H_{12}N_4$, with the structure represented by the following Chemical Formula 1, named 9-[(2R,5S)-5-(hydroxymethyl)oxolan-2-yl]-1H-purin-6-one according to the IUPAC nomenclature. The active ingredient in the pharmaceutical composition for prevention, alleviation, or treatment of neuroinflammatory disease according to one embodiment of the present disclosure may be at least one selected from the group consisting of didanosine, a derivative thereof, a metabolite, and a pharmaceutically acceptable salt thereof.

[Chemical Formula 1]

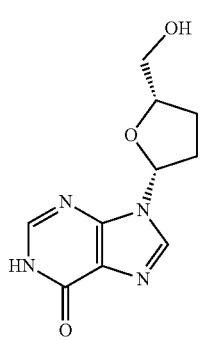

Didanosine, represented by Chemical Formula 1, may be used in the form of salts in the present disclosure. The salts may be acid addition salts formed with various pharmaceutically or sitologically acceptable organic or inorganic acids. The acid addition salts can be obtained from inorganic acids such as hydrochloric acid, nitric acid, phosphoric acid, sulfuric acid, hydrobromic acid, hydroiodic acid, nitrous acid, and phosphorous acid, and nontoxic organic acids such as aliphatic mono- and dicarboxylate, phenyl-substituted alkanoate, hydroxy alkanoate and alkanedioate, aromatic acids, and aliphatic and aromatic sulfonic acids. Such nontoxic salts may be prepared using sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propionic acid, oxalic acid, malonic acid, succinic acid, suberate, sebacate, fumarate, maleate, butyne-1,4-dioate, hexane-1,6-dioic acid, benzoic acid, chlorobenzoic acid, methylbenzoic acid, dinitrobenzoic acid, hydroxybenzoate, methoxybenzoic acid, phthalic acid, terephthalate, benzene sulfonic acid, toluene sulfonic acid, chlorobenzene sulfonic acid, xylene sulfonic acid, phenyl acetic acid, phenyl propionic acid, phenyl butyrate, citrate, lactate, β-hydroxybutyrate, glycolate, malate, tartrate, methane sulfonate, propane sulfonate, naphthalene-1-sulfonate, naphthalene-2-sulfonate, mandelate, trifluoroacetic acid, etc. as such pharmaceutically nontoxic salts.

The acid addition salt according to the present disclosure may be prepared by a typical method, for example, by dissolving the compound of Chemical Formula 1 in an excessive amount of acid aqueous solution and precipitating the salt in a water-miscible organic solvent, for example, methanol, ethanol, acetone or acetonitrile. In addition, the mixture may be dried by evaporating the solvent or the excessive amount of acid solution, followed by suction filtration of the precipitated salt.

A pharmaceutically or sitologically acceptable metal salt of didanosine represented by Chemical Formula 1 according to the present disclosure may be prepared by using a base. An alkali metal or alkaline earth metal salt is obtained for example, by dissolving the compound in an excessive amount of alkali metal hydroxide or alkaline earth metal hydroxide solution, filtering out a non-dissolved compound salt, and drying the filtrate through evaporation. In this regard, metal salts prepared with lithium, sodium, potassium, or calcium are agrochemically suitable. Moreover, silver salts corresponding thereto may be obtained by reacting alkali metal or alkaline earth metal salts with an appropriate silver salt (for example, silver nitrate).

As used herein, the term "neuroinflammatory disease" is intended to encompass all diseases caused by inflammation in the nervous system. For instance, the disease may be at least one selected from the group consisting of multiple sclerosis, neuroblastoma, stroke, dementia, Alzheimer's disease, cognitive impairment, memory impairment, disturbance of attention, Parkinson's disease, Lou Gehrig's disease, Huntington's disease, Creutzfeldt Jakob disease, post-traumatic stress disorder, depression, schizophrenia, neuropathic pain, and amyotrophic lateral sclerosis, but with no limitations thereto.

The Alzheimer's disease (AD) may comprise, for example, sporadic Alzheimer's disease (SAD) or familial Alzheimer's disease (FAD) Familial Alzheimer dementia is known to be caused mainly by mutations in PSEN gene. PSEN gene codes for the transmembrane protein presenilin, and expresses the catalytic site of gamma-secretase.

In an embodiment of the present disclosure, the disease may be hereditary dementia or familial Alzheimer's disease (FAD). More specifically, the disease may be an Alzheimer's disease or dementia related with Alzheimer's disease having a mutation in at least one gene selected from the group consisting of respective genes encoding amyloid precursor protein (APP), presenilin 1 (PSEN1), and presenilin 2 (PSEN2). The mutation in the Presenilin 2 gene may comprise at least one selected from the group consisting of A85V, N141Y, M174I, G212V, A237V, M239I and M239V, in addition to PSEN2 N141I.

The disease may be cognitive impairment, memory loss, or Alzheimer's disease or related symptoms, each caused by neuroinflammation, and may occur or worsen with aging, genetic mutation, head trauma, depression, or hypertension complications.

The neuroinflammation may be caused by at least one selected from the group consisting of genetic mutation, infection, brain trauma, and alcoholism. The genetic mutation may be a mutation in at least one selected from the group consisting of respective genes encoding amyloid precursor protein (APP), Presenilin 1 (Psen1), and Presenilin 2 (Psen2).

As used herein, the term "neuroinflammation-induced Alzheimer's disease" refers to dementia induced by artificially generating a neuroinflammatory response, and this dementia can be expressed within a short period of time, unlike the aging-induced dementia. As used herein, the term "neuroinflammation-induced Alzheimer's disease" refers to dementia induced by artificially generating a neuroinflammatory response.

More specifically, the subject and/or the disease according to the present disclosure is characterized by having at least a genetic mutation in at least one selected from Amyloid Precursor Protein (APP), Presenilin 1 (Psen1), and Psenilin 2 (Psen2), compared with a normal subject or a normal disease.

The composition according to an embodiment of the present disclosure may act to inhibit the expression of an inflammatory cytokine in the central nervous system. The inflammatory cytokine may be a neuroinflammatory cytokine.

As used herein, the term "inflammatory cytokine" refers to a cytokine involved in an inflammatory response to bacterial or viral infection, tissue injury, etc. The composition comprising didanosine or a salt thereof according to the present disclosure may inhibit the expression of the inflammatory cytokine. The inflammatory cytokine inhibited by the present disclosure may be particularly IL-6, but is not limited thereto. Without being bound to a specific theory, levels of inflammatory cytokines may be increased in neuroinflammatory diseases and the suppression of neuroinflammatory cytokines such as IL-6, etc. can treat and alleviate neuroinflammatory diseases such as Alzheimer's disease. Therefore, didanosine or a salt thereof according to the present disclosure recovers a damaged transcriptional activator and inhibits the expression of an inflammatory cytokine, thus can be usefully used in the treatment of neuroinflammatory diseases comprising Alzheimer's disease.

In the following Examples, a composition comprising didanosine or a salt thereof as an active ingredient according to the present disclosure was found to have a prophylactic, improving, or therapeutic effect on Alzheimer's disease as demonstrated through its anti-inflammatory activity in animal models in which neuroinflammatory cytokines responsible for microglial neuroinflammation were prevented from being expressed thereby.

According to an Example of the present disclosure, treatment with didanosine was measured to significantly decrease the release of IL-6 in primary microglia of Alzheimer animal models (see Example 6) and be almost free of cytotoxicity (see Example 5).

It was also observed in the Example of the present disclosure that when didanosine was treated to microglia derived from mouse models of neuroinflammatory disease, e.g., neuroinflammatory Alzheimer's disease, it was confirmed that the anti-inflammatory and memory recover effects appeared by suppressing the expression of inflammatory cytokines. Therefore, the composition according to an embodiment of the present disclosure may inhibit the expression of a neuroinflammatory cytokine in microglia. The microglia may have at least a genetic mutation in at least one selected from the group consisting of amyloid precursor protein (APP), Presenilin 1 (PSEN1), and Presenilin 2 (PSEN2). In addition, the composition according to an embodiment of the present disclosure may be a composition for improving memory.

In detail, leading to the present disclosure, intensive and thorough research, conducted by the present inventors into a substance that can treat a neuroinflammatory disease by regulating the expression of an inflammatory cytokine involved in a microglial inflammatory response, resulted in the finding that the application of didanosine to microglia in PSEN2 N141I KI/+ mouse models of Alzheimer's disease elicited an anti-inflammatory effect and promoted amyloid-beta degradation through repression of the expression of the inflammatory cytokine IL-6. Furthermore, didanosine was identified to recover a cognitive function from a declined state in 5×FAD mouse which is a different model of Alzheimer's disease.

As used herein, the term "PSEN2 gene" refers to a gene coding for a PSEN2 polypeptide. The PSEN2 gene comprises NCBI reference sequence NC_000001.11 (226870594 . . . 226903829) for human PSEN2 gene and NC_000067.7 for mouse PSEN2 gene, and orthologs known in the art. The term "PSEN2 polypeptide" refers to a polypeptide located at the NCBI reference sequence NP_000438.2 for human PSEN2 protein and at the NCBI reference sequence NP_001122077 for mouse PSEN2 protein, and is intended to encompass orthologs thereof.

Known as PSEN2 gene mutations associated with neuroinflammation and/or Alzheimer's disease are A85V, N141I, N141Y, M174I, G212V, A237V, M239I, and M239V, and at least one of the mutations may be included (Jiang et al., "A Review of the Familial Alzheimer's Disease Locus PRESENILIN 2 and Its Relationship to PRESENILIN 1." Journal of Alzheimer's Disease 66 (2018) 1223-1339).

In the following Examples, treatment with didanosine was observed to exhibit an anti-inflammatory effect and a memory recovery effect on Psen2 N141I knock-in (KI) animal models in which isoleucine (I) was substituted for the amino acid residue arginine (N) at position 141 in the presenilin 2 gene as an example of familial Alzheimer's disease.

Therefore, according to another aspect of the present disclosure is drawn to an anti-inflammatory composition comprising didanosine or a pharmaceutically acceptable salt thereof.

Therefore, according to another aspect of the present disclosure is drawn to a composition comprising didanosine or a pharmaceutically acceptable salt thereof for improving memory.

Based on the data of the following Examples demonstrating the alleviative effect of didanosine on neuroinflammatory responses in animal models or microglial cells thereof and didanosine is known to be able to cross the blood-brain barrier, the composition according to the present disclosure can be advantageously used as a pharmaceutical composition or a health functional food composition for alleviation or treatment of neuroinflammatory disease.

A still aspect of the present disclosure is drawn to a composition comprising didanosine or a pharmaceutically acceptable salt thereof for promoting degradation of microglial amyloid beta. A still further aspect of the present disclosure pertains to a use of the pharmaceutical composition for promoting degradation of amyloid beta in microglia, comprising didanosine or a pharmaceutically acceptable salt thereof. A still another aspect of the present disclosure pertains to a pharmaceutical composition for use in promoting degradation of amyloid beta in microglia, comprising didanosine or a pharmaceutically acceptable salt thereof.

The microglia of in the ability to degrade amyloid beta may have decreased due to neuroinflammation.

The microglia may comprise at least a genetic mutation in at least one selected from the group consisting of amyloid precursor protein (APP), Presenilin 1 (PSEN1), and Presenilin 2 (PSEN2). By way of example, the microglia may comprise a Presenilin 2 gene mutation and specifically, may be Psen2 N141I KI/+ microglia.

In the following Examples, microglia, when treated with didanosine, were observed to recover from the decreased ability to degrade amyloid beta. Hence, the composition according to an aspect of the present disclosure may recover microglial ability to degrade amyloid beta.

An additional aspect of the present disclosure is drawn to a food composition comprising didanosine or a sitologically acceptable salt thereof for prevention or improvement of neuroinflammatory disease. The food may be a health functional food. In this regard, didanosine and the neuroinflammatory disease are as described above.

When the composition according to the present invention is in the form of a health functional food composition, it can be processed into foods with high medical and medicinal effects to efficiently exhibit bioregulatory functions in addition to foods for specific health purposes and nutritional supply. The foods may be used as functional foods, health foods, and health supplements in combination according to some cases, and may be formulated into various forms, such as tablets, capsules, powders, granules, liquids, pills, etc., to obtain useful effects.

The health functional composition of the present disclosure may further comprise additional ingredients that are commonly used in food compositions to improve an odor, taste, visual appearance, etc., for example, vitamins A, C, D, E, B1, B2, B6, B12, niacin, biotin, folate, pantothenic acid, etc. Also, the composition may comprise minerals, such as zinc (Zn), iron (Fe), calcium (Ca), chromium (Cr), magnesium (Mg), manganese (Mn), copper (Cu), etc. Additionally, amino acids, such as lysine, tryptophan, cysteine, valine, etc., may be comprised in the composition. Food additives available for the composition comprise preservatives (e.g., potassium sorbate, sodium benzoate, salicylic acid, sodium dehydroacetate, etc.), disinfecting agents (e.g., bleaching powder and higher bleaching powder, sodium hypochlorite, etc.), antioxidants (e.g., butylhydroxyanisole (BHA), butylhydroxytoluene (BHT), etc.), colorants (e.g., tar dye, etc.), color fixing agents (e.g., sodium nitrite, sodium nitrite etc.), bleaching agents (e.g., sodium sulfite), seasoning agents (e.g., MSG, sodium glutamate, etc.), sweeteners (e.g., dulcin, cyclamate, saccharin, sodium, etc.), fragrances (e.g., vanillin, lactones, etc.), blowing agents (e.g., alum, potassium D-bitartrate, etc.), fortifying agents, emulsifiers, thickeners, coating agents, gum bases, antifoaming agents, solvents, and improving agents. The additives may be selected according to the type of foods and may be used in suitable amounts.

When used as a food additive, the health functional food of the present disclosure may be added as it is or used together with a different food or food ingredients, and it can be appropriately used according to a conventional method.

In the health functional food of the present disclosure, the content of didanosine is not particularly limited and may vary depending on the condition of the target subjects and the type and progression of concrete diseases. Didanosine may be contained in the total amount of the food, as necessary.

A further additional aspect of the present disclosure is drawn to a method for treating a neuroinflammatory disease, the method comprising a step of administering the pharmaceutical composition into a subject. The neuroinflammatory disease is as described above.

In the present disclosure, the "subject" may be mammals such as mice, domestic animals, rats, humans, etc., particularly, companion dogs, racehorses, humans, etc. in need of the treatment of the neuroinflammatory disease such as Alzheimer's disease, preferably humans.

The pharmaceutical composition of the present disclosure may be administered orally or parenterally (e.g., intravenously, subcutaneously, intraperitoneally, or topically) according to a desired method, and the dose may vary depending on the state and body weight of the subject, the severity of disease, drug form, and the route and duration of administration, and can be selected appropriately by a person skilled in the art.

The pharmaceutical composition of the present disclosure may be administered in a pharmaceutically effective amount. As used herein, the term "pharmaceutically effective amount" refers to an amount sufficient for the treatment of diseases at a reasonable benefit/risk ratio applicable to medical treatment, and the level of the effective dose may be determined based on the factors comprising the kind and severity of illness, drug activity, drug sensitivity, administration time, administration route and excretion rate, length of treatment, factors including a drug to be used simultaneously, and other factors well known in the medical field. The composition of the present disclosure may be administered as an individual therapeutic agent, in combination with another therapeutic agent, and sequentially or simultaneously with a conventional therapeutic agent, and may be administered once or multiple times. It is important that the pharmaceutical composition be administered in the minimum amount that can obtain the maximum effect without adverse effects considering all of the factors described above, and it can be determined by one of ordinary skill in the art.

Specifically, the effective amount of the pharmaceutical composition of the present disclosure may be dependent on a subject's age, sex, condition, body weight, an absorption rate of the active ingredient in the body, an inactivation rate, an excretion rate, a type of disease, or a drug used in combination, and may be generally administered at 0.001 to 4 mg per 1 kg of body weight daily or every other day, or divided into one or three daily administrations. However, the effective amount may vary depending on an administration route, sex, body weight, age, etc., and therefore the scope of the present disclosure is not limited by the dose in any way.

For instance, the composition according to an embodiment of the present disclosure may be administered at a dose less than the effective amount of didanosine administered as an HIV therapeutic agent, or at a dose of 0.9 times or less, 0.8 times or less, 0.7 times or less, 0.6 times or less, 0.5 times or less, 0.4 times or less, 0.3 times or less, 0.2 times or less, 0.1 times or less, 0.09 times or less, 0.08 times or less, 0.07 times or less, 0.06 times or less, 0.05 times or less, 0.04 times or less, 0.03 times or less, 0.02 times or less, or 0.01 times or less of the effective amount of didanosine administered as an HIV therapeutic agent. In this regard, even if the lower limit of the dose is not specified, those skilled in the art will be able to clearly practice the present disclosure for the prevention or treatment of neuroinflammatory diseases. For example, the lower limit of the dose may be 0.0001 times or more, 0.0005 times or more, 0.001 times or more, 0.005 times or more, 0.01 time or more, 0.05 times or more, or 0.1 times or more of the effective amount of didanosine administered as an HIV therapeutic agent, but is not limited thereto.

For example, the composition according to an aspect of the present disclosure may be administered at a daily dose of 0.001 to 4 mg/kg, 0.001 to 3 mg/kg, 0.001 to 2.5 mg/kg, 0.001 to 2 mg/kg, 0.001 to 1.5 mg/kg, 0.001 to 1 mg/kg, 0.001 to 0.9 mg/kg, 0.001 to 0.8 mg/kg, 0.001 to 0.7 mg/kg, 0.001 to 0.6 mg/kg, 0.001 to 0.5 mg/kg, 0.001 to 0.45 mg/kg, 0.001 to 0.4 mg/kg, 0.005 to 4 mg/kg, 0.005 to 3 mg/kg, 0.005 to 2.5 mg/kg, 0.005 to 2 mg/kg, 0.005 to 1.5 mg/kg, 0.005 to 1 mg/kg, 0.005 to 0.9 mg/kg, 0.005 to 0.8 mg/kg, 0.005 to 0.7 mg/kg, 0.005 to 0.6 mg/kg, 0.005 to 0.5 mg/kg, 0.005 to 0.45 mg/kg, 0.005 to 0.4 mg/kg, 0.01 to 4 mg/kg, 0.01 to 3 mg/kg, 0.01 to 2.5 mg/kg, 0.01 to 2 mg/kg, 0.01 to 1.5 mg/kg, 0.01 to 1 mg/kg, 0.01 to 0.9 mg/kg, 0.01 to 0.8 mg/kg, 0.01 to 0.7 mg/kg, 0.01 to 0.6 mg/kg, 0.01 to 0.5 mg/kg, 0.01 to 0.45 mg/kg, 0.01 to 0.4 mg/kg, 0.1 to 4 mg/kg, 0.1 to 3 mg/kg, 0.1 to 2.5 mg/kg, 0.1 to 2 mg/kg, 0.1 to 1.5 mg/kg, 0.1 to 1 mg/kg, 0.1 to 0.9 mg/kg, 0.1 to 0.8 mg/kg, 0.1 to 0.7 mg/kg, 0.1 to 0.6 mg/kg, 0.1 to 0.5 mg/kg, 0.1 to 0.45 mg/kg, or 0.1 to 0.4 mg/kg.

As used herein, the term "prevention" refers to all actions of inhibiting a neuroinflammatory disease or delaying the onset thereof by administration of the pharmaceutical composition according to the present disclosure.

As used herein, the term "improvement" refers to all types of actions that reduce a degree of symptoms of neuroinflammatory disease by administration of the pharmaceutical composition according to the present disclosure.

The term "treatment", as used herein, refers to all actions involved in improving or beneficially changing symptoms of neuroinflammatory disease by administration of the pharmaceutical composition according to the present disclosure. Specifically, the term "treatment" comprises the decrease or alleviation of at least one symptom associated or caused by the state, disorder or disease being treated. The treated subject may exhibit partial or entire alleviation of a symptom (e.g., Alzheimer's disease or related pathology) or the symptom may remain stagnant after the treatment according to the present disclosure. The term "treatment" is intended to encompass prophylaxis, therapy and cure.

When used in the form of a pharmaceutical composition, the composition according to the present disclosure may comprise an effective amount of didanosine alone or in combination of a pharmaceutically acceptable carrier. In this regard, so long as it is used typically used for formulation, any pharmaceutically acceptable carrier may be available in the present disclosure, and comprise lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, but are not limited thereto. In addition to the above components, the composition may further comprise a lubricant, a humectant, a sweetener, a flavorant, an emulsifier, a suspending agent, a preservative, and so on.

A still additional aspect of the present disclosure is drawn to a use of the pharmaceutical composition for preventing or treating a neuroinflammatory disease. The pharmaceutical composition and the neuroinflammatory disease are as described in the foregoing.

A yet another aspect of the present disclosure is drawn to a use of the pharmaceutical composition for producing a pharmaceutical composition for prevention or treatment of a neuroinflammatory disease. The pharmaceutical composition and the neuroinflammatory disease are as described in the foregoing.

A yet further aspect of the present disclosure is drawn to a pharmaceutical composition for use in preventing or treating a neuroinflammatory disease. The pharmaceutical composition and the neuroinflammatory disease are as described in the foregoing.

Advantageous Effects

With the ability to inhibit the expression of neuroinflammatory cytokines, a composition according to an aspect of the present disclosure was identified to be effective for preventing or treating a neuroinflammatory disease and improve cognitive function in Alzheimer's disease mice, and thus is expected to find advantageous applications in the development of substances for medicinal products and quasi-drug products and related industries.

Being able to inhibit the expression of neuroinflammatory cytokines, promote the degradation of amyloid beta, and improve cognitive functions in Alzheimer's disease animal models, a composition according to an aspect of the present disclosure was identified to effectively prevent or treat a neuroinflammatory disease and as such, is expected to find advantageous applications in the development of substances for medicinal products and quasi-drug products and related industries.

However, the advantages of the present disclosure are not limited to those described in the foregoing, and it should be understood to include all effects that can be inferred from the elements of the invention described in the detailed description or the claims appended.

BRIEF DESCRIPTION OF THE DRAWINGS

FIG. 1A is a schematic view of a strategy for targeted insertion of N141I point mutation; and FIG. 1B depicts Sanger sequencing chromatograms of normal (wild-type), KI/+, KI/KI mouse.

FIG. 2A shows blood IL-6 concentration in animals in which neuroinflammation has been induced by intraperitoneal injection of various concentrations of lipopolysaccharide (LPS). The Psen2 mutation Alzheimer's disease mice overexpressed IL-6 at all LPS concentrations injected thereto via an intraperitoneal route, with the expression difference between normal and Alzheimer' disease models being more pronounced at lower concentrations; FIG. 2B shows the production of TNF-α in response to intraperitoneal injection of LPS, with similar blood levels between normal and Psen2 N141I mutation Alzheimer's disease mice at all concentrations; and FIG. 2C shows blood concentrations of the inflammatory cytokines IL-6, CXCL1, CCL2, and CCL5. The levels of the inflammatory cytokines were remarkably increased only in the Psen2 N141I mutation mice upon injection of LPS at a low concentration (0.35 μg/kg) which does not induce any inflammatory response in wild-type mice.

FIG. 4A shows a memory decline in the neuroinflammation-induced Psen2 N141I mutation mice as measured by Y-maze assay; FIG. 4B shows no difference in locomotor activity between the mice as measured by Y-maze assay; FIG. 4C is a schematic view of T-maze assay methods; and FIG. 4D is a graph of T-maze assay results showing a memory decline in the neuroinflammation-induced Psen2 N141I mutation mice in terms of a remarkable decrease in success rate.

MODE FOR INVENTION

Below, a better understanding of the present disclosure may be obtained through the following examples, which are set forth to illustrate, but are not to be construed to limit the present disclosure.

Example 1. Construction of Animal Model of Disease

All protocols for the care and use of animals were approved by and in accordance with the guidelines established by the Institutional Animal Care and Use Committee of DGIST. Animals were maintained in a specific pathogen-free environment under a standard 12-h light/12-h dark cycle at the DGIST animal facility.

To more accurately reproduce a human neuroinflammatory disease, e.g., human Alzheimer's disease and maintain the endogenous expression level, heterozygous $Psen2^{N141I/+}$ (KI/+) mice were used. $Psen2^{N141I/+}$ mice were generated using homologous recombination.

Specifically, construction was made of a Psen2 N141I knock-in (KI) animal model of familial Alzheimer's disease in which arginine (N) at position 141 in the presenilin amino acid sequence was substituted by isoleucine (I). Targeting vector included the I141 mutation in exon 4 and the Neo'-loxp sequence, and the homologous region in the targeting vector was inserted into Psen2 of the wild-type (WT) allele. $Psen2^{N141I/N141I}$; loxp-Neo'-loxp mice were crossed with Cre mice using the Cre-loxp system to generate knock-in mice carrying the Psen2 N141I mutation.

In the Example, "Psen2 N141I" refers to a substitution in the normal Psen2 gene of animal models for expressing the same mutation as a dementia mutation reported for humans and more specifically to the substitution of the amino acid I for the amino acid N at position 141 in the murine Presenilin 2 gene. In the present disclosure, the gene carrying Psen2 N141I is represented by the polynucleotide of SEQ ID NO: 1 while the wild-type Psen2 gene is given as SEQ ID NO: 2.

Figure 1A:
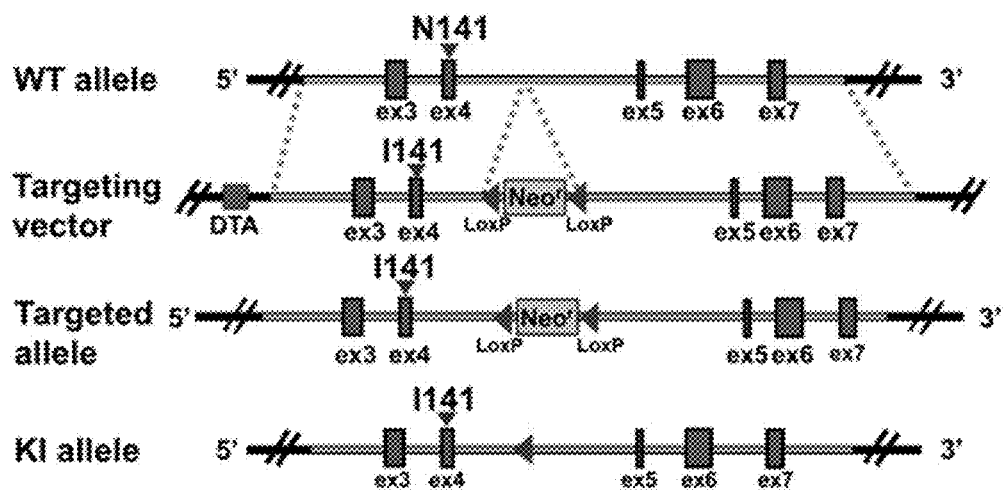
FIG. 1A and FIG. 1B illustrate the construction of Psen2 N141I mutation Alzheimer's disease mouse models according to an embodiment of the present disclosure.
Figure 1B:
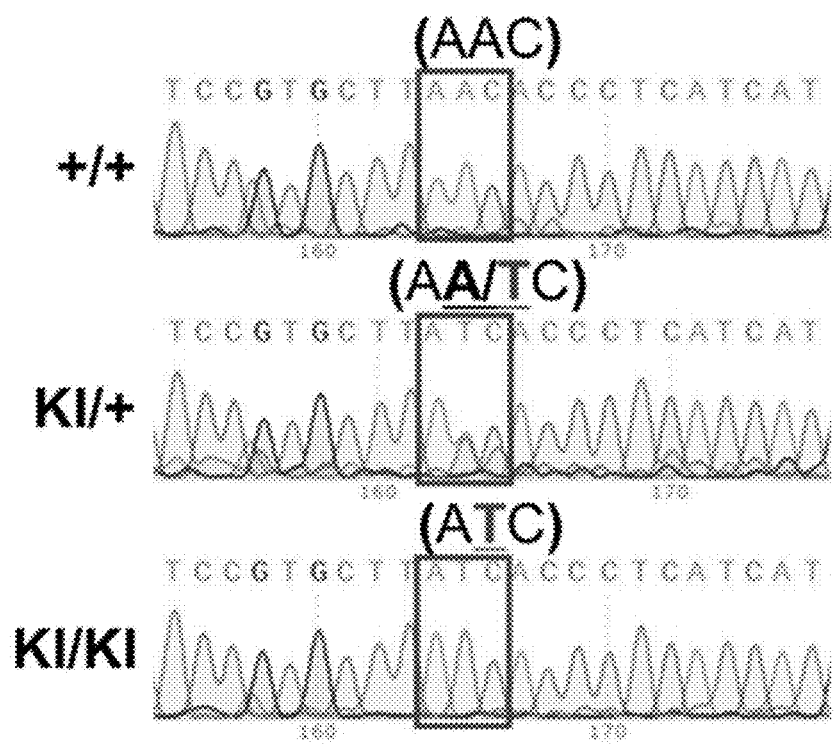

KI mice harboring the Psen2 N141I allele ($Psen2^{N141I/+}$ and $Psen2^{N141I/N141I}$) were generated as illustrated in FIG. 1A. As shown in FIG. 1B, the substitution of AAC to ATC at Asparagine (N) resulted in KI/+ models with asparagine (N) and isoleucine (I) and KI/KI models in which both the alleles were substituted to ATC (I141) as confirmed by genomic sequencing.

Example 2. LPS-Induced Inflammation in Animal Model of Disease

This example was designed to confirm that the Psen2 N141I mutation Alzheimer's disease mouse models exhibit hyperimmune responses compared to normal (wild-type) mice.

2-1. Assay for LPS Concentration to Induce Inflammation

To examine whether the $Psen2^{N141I/+}$ mice tended to exhibit inflammation and cognitive impairment as the immune response of the microglia derived therefrom was aggravated, comparison was made of immune responses between wild-type and $Psen2^{N141I/+}$ mice at various concentration of LPS.

In mice, the immune response peaks in the hours around the beginning of the active phase. Therefore, wild-type and $Psen2^{N141I/+}$ mice were intraperitoneally (i.p.) injected with LPS at 18:00 (Zeitgeber time, light-on at 07:00 and light-off at 19:00) and monitored for the inflammatory response after 20 hours, that is, at 14:00 next day. The LPS, which acts as a ligand to toll-like receptor 4 to induce cellular immune responses, was derived *Escherichia coli* O111:B4. LPS was diluted in phosphate-buffered saline (PBS) according to predetermined concentrations and 100 μL each was injected into mice via an intraperitoneal route.

Specifically, LPS intraperitoneal injections at concentrations of 1.4, 3.6, 4.0, 25, and 5,000 μg/kg induced neuroinflammation in the Psen2 N141I mutation Alzheimer's disease mouse models obtained in Example 1.

For a comparison experiment, wild-type mouse models, instead of the Alzheimer's disease mouse models, were injected with the same concentrations of LPS for neuroinflammatory tests. In other comparative tests, wild-type mouse and Psen2 N141I mutation Alzheimer's disease mouse models without LPS injections were prepared. That is, wild-type mice without LPS injection (WT(LPS(−))) were assigned to group 1, wild-type mice with various concentration of LPS injected thereto (WT(LPS(+))) to group 2, Alzheimer's disease mouse models without LPS injection (KI/+(LPS(−))) to group 3, and Alzheimer's disease mouse models with various concentration of LPS injected thereto (KI/+(LPS(+))) to group 4, each consisting of 5-8 mice.

To investigate neuroinflammatory responses to various concentration of LPS injection, blood was extracted from cheek veins of the wild-type mice of group 2 and the Alzheimer's disease mouse models of group 4 at 20 hours after injection of LPS. Sera obtained by centrifuging the blood samples were measured for levels of IL-6, TNFα, CCL2, CXCL1, and CCL5 using an ELISA kit (R&D Systems) according to the manufacturer's instruction. In addition, sera were extracted from the wild-type without LPS injection of group 1 and the Psen2 N141I mutation Alzheimer's disease mouse models of group 3 in the same manner and measured for levels of the proteins using the ELISA kit according to the manufacturer's instruction.

IL-6 and TNF-α levels analyzed in sera from the mice of groups 1 to 4 are summarized in Table 1, below.

TABLE 1

| LPS Concentration (μg/kg) | | 1.4 | 3.6 | 4.0 | 25 | 5000 |
|---|---|---|---|---|---|---|
| Group 1-<br>WT(LPS(−)) | IL-6<br>(pg/mL) | 55.983 ± 5.891 | 6.167 ± 2.833 | 26.815 ± 6.121 | 152.718 ± 7.843 | 47.066 ± 4.710 |
| | TNF-α<br>(pg/mL) | 57.129 ± 15.581 | 51.606 ± 16.486 | 13.801 ± 6.203 | 7.112 ± 2.436 | 59.262 ± 18.848 |
| Group 2-<br>WT(LPS(+)) | IL-6<br>(pg/mL) | 135.414 ± 12.377 | 435.609 ± 58.851 | 589.102 ± 31.891 | 2186.084 ± 152.786 | 3362.240 ± 261.326 |
| | TNF-α<br>(pg/mL) | 95.940 ± 15.385 | 212.951 ± 57.449 | 127.232 ± 32.518 | 844.100 ± 52.867 | 1549.235 ± 124.825 |
| Group 3-<br>KI/+(LPS(−)) | IL-6<br>(pg/mL) | 65.998 ± 13.677 | 6.167 ± 2.833 | 14.302 ± 5.915 | 180.661 ± 7.031 | 54.023 ± 6.36 |
| | TNF-α<br>(pg/mL) | 35.391 ± 13.406 | 21.775 ± 9.850 | 19.633 ± 6.349 | 9.389 ± 2.097 | 88.176 ± 18.527 |
| Group 4-<br>KI/+(LPS(+)) | IL-6<br>(pg/mL) | 260.651 ± 28.433 | 858.809 ± 45.574 | 884.273 ± 27.475 | 3180.879 ± 95.747 | 4596.187 ± 136.528 |
| | TNF-α<br>(pg/mL) | 93.490 ± 24.912 | 218.504 ± 666.226 | 157.121 ± 13.298 | 874.443 ± 65.026 | 1736.561 ± 19.360 |

In Table 1, data for blood L-6 and TNF-α levels of each group are mean±SEM. The wild-type mice of group 2 and the Alzheimer's disease mouse models of group 4, which were both injected with LPS, both overexpressed IL-6, with the expression difference therebetween gradually increasing at lower concentrations. In response to LPS, the wild-type mice and the Alzheimer's disease mouse models exhibited the same blood TNF-α levels. The wild-type mice in group 1 and the Psen2 N141I mutation Alzheimer's disease mouse models in group 3, which had not been injected with LPS, both exhibited same excretion of IL-6 and TNF-α at very low levels.

Figure 2A:
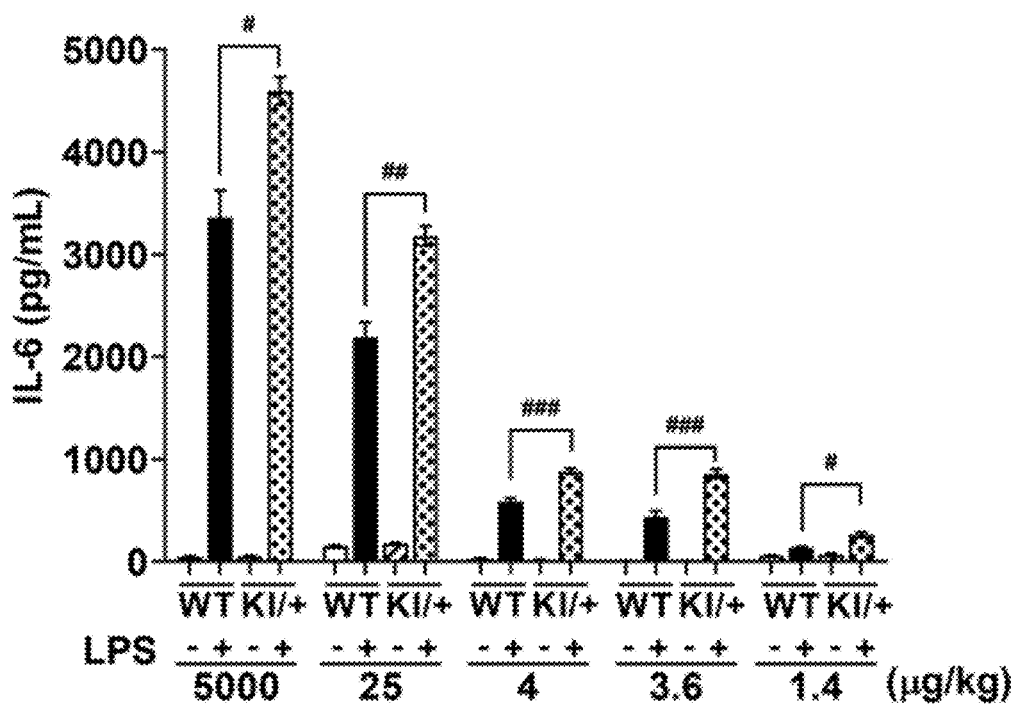
FIG. 2A to FIG. 2C show overactive inflammatory responses in the Psen2 N141I mutation Alzheimer's disease mouse models compared to normal (wild-type) mouse according to an embodiment of the present disclosure.
Figure 2B:
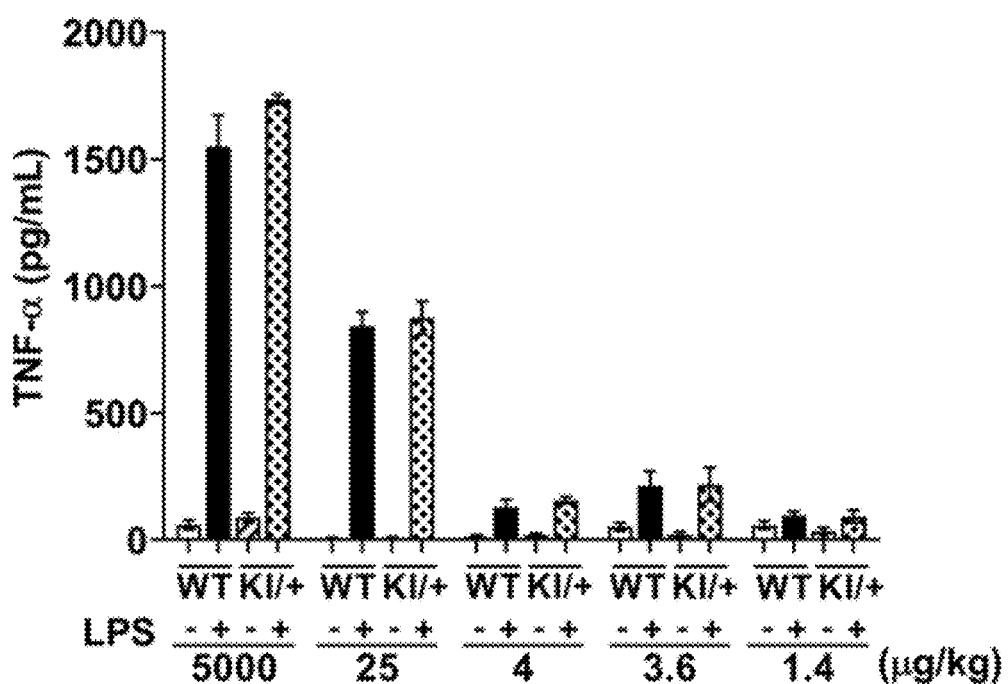

As shown in FIG. 2A, compared with wild-type mice, KI/+ mice exhibited a higher circulating level of IL-6 at all LPS concentration tested, and the relative difference between the genotypes was more pronounced at the lower concentrations. The blood levels of TNF-α were the same in both genotypes at all concentrations as can be seen in FIG. 2B.

2-2. Inflammation Induced by Treatment with Low Concentration of LPS in Disease Animal Animals of groups 1 to 4 were prepared in the same manner as in Example 2-1, but for injecting LPS at a low concentration (0.35 μg/kg) insufficient to induce inflammatory responses in the wild-type mice, instead of the various concentrations.

Sera were extracted in the same manner from the mouse models and measured for protein levels using an ELISA kit according to the manufacturer's instructions. Blood levels of the inflammatory cytokines IL-6, CXCL1, CCL2, and CCL5 in sera from the mice of groups 1 to 4 are summarized in Table 2, below.

TABLE 2

| Inflammatory cytokine secretion | IL-6 (pg/mL) | CXCL1 (pg/mL) | CCL2 (pg/mL) | CCL5 (pg/mL) | TNF-α (pg/mL) |
|---|---|---|---|---|---|
| Group 1- WT(LPS(−)) | 59.231 ± 11.121 | 290.073 ± 47.194 | 49.908 ± 14.051 | 81.978 ± 13.271 | 65.792 ± 9.335 |
| Group 2- WT(LPS(+)) | 60.385 ± 8.520 | 298.861 ± 27.363 | 63.494 ± 17.542 | 108.104 ± 24.672 | 58.332 ± 7.341 |
| Group 3- KI/+(LPS(−)) | 47.048 ± 11.825 | 252.408 ± 38.448 | 66.926 ± 24.473 | 99.095 ± 28.489 | 64.929 ± 3.615 |
| Group 4- KI/+(LPS(+)) | 190.945 ± 28.265 | 447.010 ± 13.464 | 263.378 ± 15.024 | 244.741 ± 36.921 | 69.896 ± 7.249 |

In Table 2, blood levels of the inflammatory cytokines IL-6, CXCL1, CCL2, and CCL5 are listed (mean±SEM). The lowest LPS concentration (0.35 μg/kg) of LPS which did not elicit immune responses in the wild-type mice of group 2 was observed to remarkably increase levels of the inflammatory cytokines only in the Psen2 Alzheimer's disease mice of group 4, unlike TNF-α.

Figure 2C:
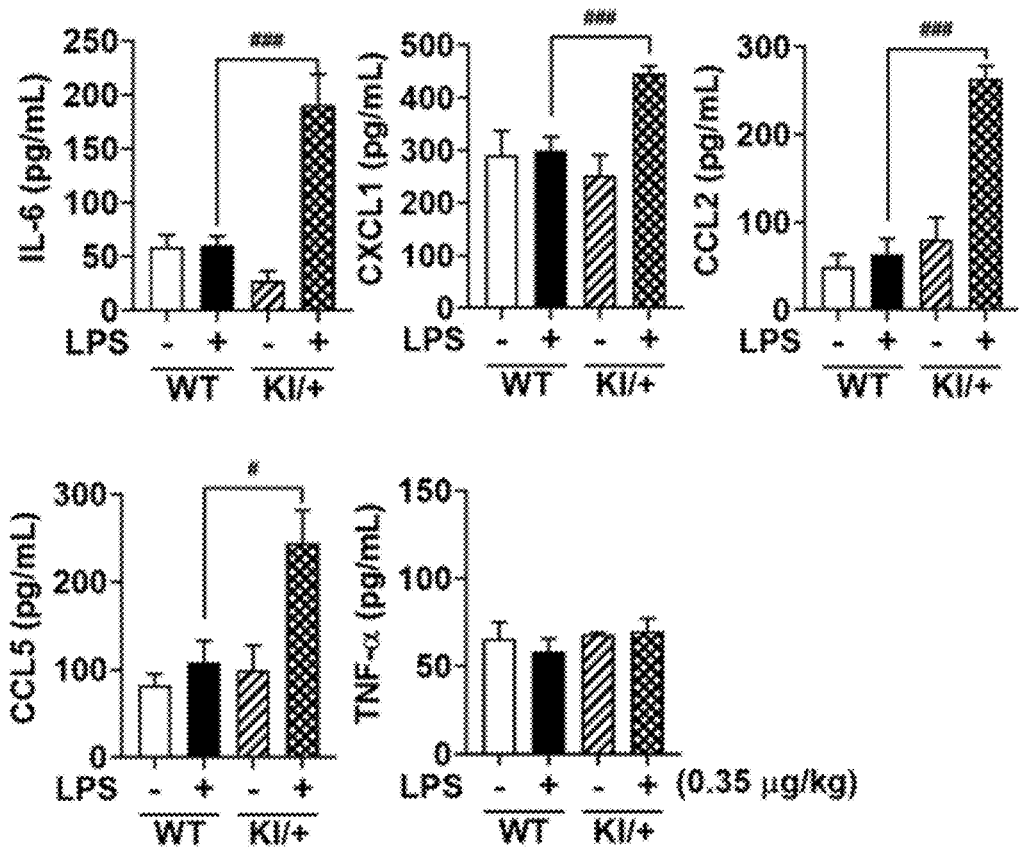

As shown in FIG. 2C, the lowest LPS concentration (0.35 μg/body weight kg) did not cause inflammation in wild-type mice, but increased blood levels of the inflammatory cytokines (IL-6, CXCL1, CCL2, and CCL5) in Psen2 Alzheimer's disease mice.

Example 3: Identification of Inflammatory Aggravation of Neuroinflammatory Animal Model by Analysis of Microglial Morphology Microglia morphology is closely related to their function and microglial activation is characterized by cell shape change. To investigate whether the increased production of inflammatory cytokines is associated with changes in the morphology in KI/+ microglia, examination was made of microglia shapes in the hippocampus of wild-type and Psen2 mutation Alzheimer's disease mice by immunohistochemical analyses with an antibody against the microglia-specific marker IBA-1.

Immunohistochemical and confocal analyses were conducted on the mice of groups 1 to 4 prepared in Example 2-2. The LPS concentration injected into groups 2 and 4 was ineffective to induce an inflammatory response in the wild-type mice (0.35 μg/kg).

For immunohistochemistry analysis, mice were anesthetized by injection of a mixture of Zoletil (Virbac, 50 mg/kg) and Rompun (Bayer, 10 mg/kg). Then, the mice were perfused with PBS, followed by 4% paraformaldehyde (PFA) for fixation. Brains were collected, post-fixed in 4% PFA for 16 hours, transferred to 30% sucrose until they sank to the bottom of the tube, and stored by using frozen solution. The brain samples were cut into 50-μm-thick coronal sections. The slices were incubated at 95° C. for antigen retrieval and then treated with IBA-1 antibody (1:250) in PBS containing 3% bovine serum albumin for 24 hours at 4° C. and then treated with secondary antibody for 2 hours at room temperature. Images were acquired with LSM 7 and LSM 700 confocal laser scanning microscope.

Figure 3A:
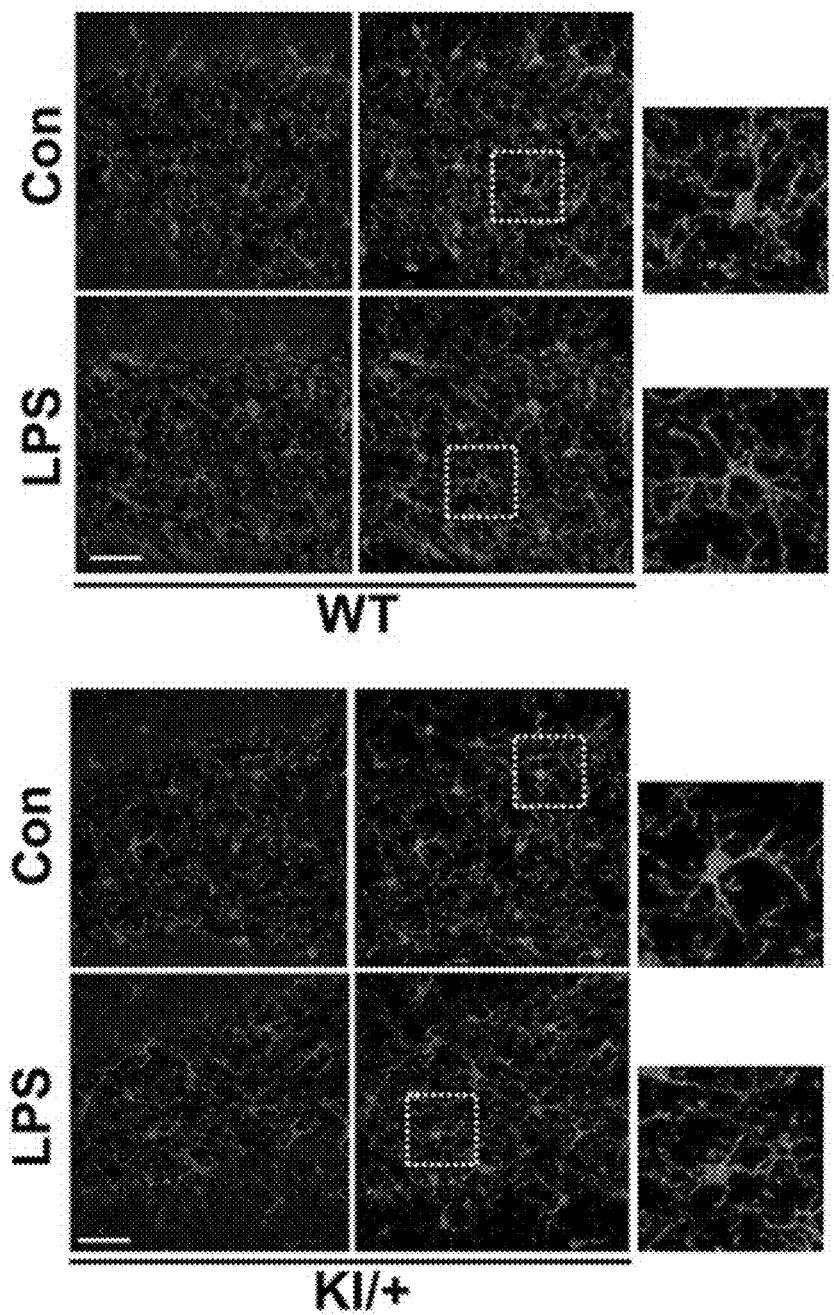
FIG. 3A shows immunofluorescent images by Iba-1 (microglial marker antibody) staining in the hippocampus of normal and Psen2 N141I mutation Alzheimer's disease mice.

As shown in FIG. 3A, hippocampal microglia in the wild-type mice of group 1 had a small cell body with highly ramified processes. Consistent with no induction of cytokine release, a low concentration of LPS did not change their morphology. On the other hand, hippocampal microglia in Psen2 mutation Alzheimer's disease mice of group 3, even in the absence of LPS injection, already had a round enlarged soma with shorter processes, and these morphological features were furthered by LPS injection in group 4.

Figure 3B:
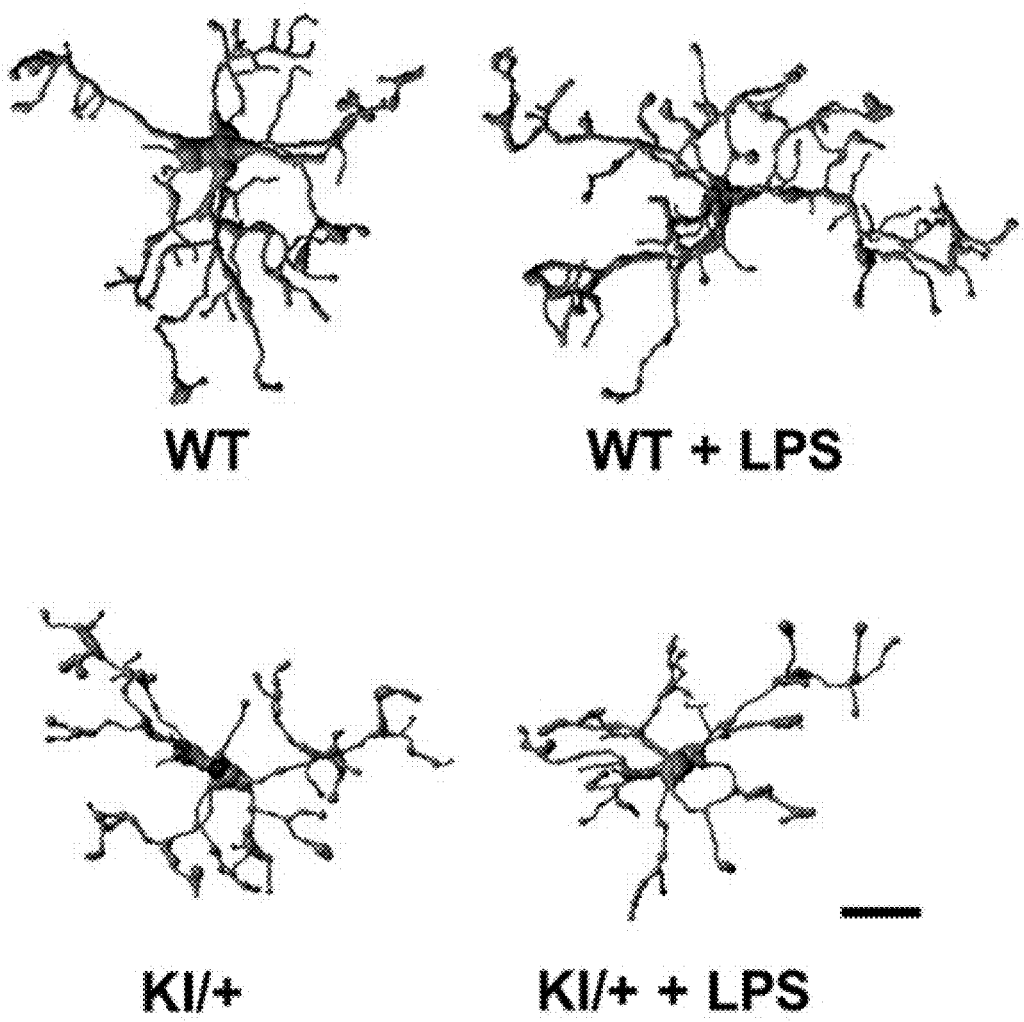
FIG. 3B shows 3D filament tracking images of Iba-1 signals made by IMARIS software.

As shown in FIG. 3B, confocal images of hippocampal microglia of the mice in groups 1 to 4 were reconstructed into their 3D morphology and measured for morphological parameters using IMARIS software. In detail, confocal images were obtained along the entire Z-axis of a randomly selected field. Then, 3D images were reconstructed from confocal images using IMARIS software (version 9.2.1, Bitplane AG).

TABLE 3

| IMARIS analysis | Dendrite length (μm) | Dendrite branch point |
| --- | --- | --- |
| Group 1- WT(LPS(−)) | 679.113 ± 38.931 | 88.226 ± 16.285 |
| Group 2- WT(LPS(+)) | 774.000 ± 38.151 | 81.161 ± 13.253 |
| Group 3- KI/+(LPS(−)) | 531.981 ± 31.526 | 44.645 ± 3.416 |
| Group 4- KI/+(LPS(+)) | 420.806 ± 21.694 | 35.871 ± 2.186 |

In Table 3, data for dendrite lengths and dendrite branch points are summarized (mean±SEM).

Figure 3C:
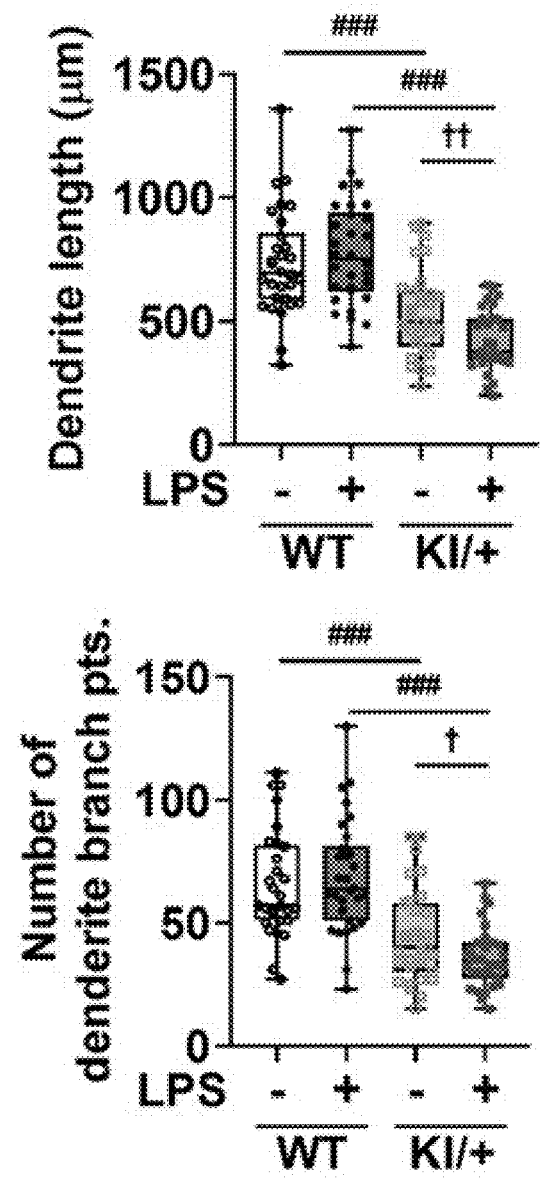
FIG. 3C shows dendrite lengths and number of branch points, as analyzed by FilamentTracker of IMARIS software. Through this, Psen2 N141I mutation Alzheimer's disease mice undergo overactive immune response by producing inflammatory cytokines in response to a low con centration of inflammatory stimulus.

As shown in FIG. 3C, the total dendrite length and the number of dendrite terminal points of each microglial cell were further reduced in the Alzheimer's disease mice of groups 3 and 4 than in the wild-type mice of groups 1 and 2 by LPS injection. It was confirmed from the data that, on the basis of morphology, microglial activation was evident in Psen2 mutation Alzheimer's disease mice and was further induced by mild LPS injection.

Example 4. Memory Decline of Neuroinflammatory Animal Model 4-1. Y-Maze Assay

To examine the spatial learning and memory of the mice of groups 1 to 4 prepared in Example 2-2, Y-maze tests were conducted 20 hours after LPS injection. The mice were injected at the low concentration of LPS (0.35 μg/kg) that does not induce an inflammatory response in wild-type mice.

Specifically, Y-maze was used to evaluate spatial working memory. The assay was conducted in white plastic arms of a Y-shaped maze. A mouse was placed in the center and was allowed to freely explore the arms for 5 min. The experiment was recorded with EthoVision software 11.5 (Noldus). The number of arm entries and the number of triads were analyzed to calculate the percentage of alternation by dividing the number of three consecutive arm entries by the number of possible triads×100 (total arm entries−2).

TABLE 4

| Y-maze | Alternation percent | No. of Arm entry |
| --- | --- | --- |
| Group 1- WT(LPS(−)) | 65.120 ± 4.161 | 16.769 ± 1.574 |
| Group 2- WT(LPS(+)) | 66.124 ± 4.441 | 14.923 ± 1.129 |
| Group 3- KI/+(LPS(−)) | 61.475 ± 4.855 | 15.417 ± 1.209 |
| Group 4- KI/+(LPS(+)) | 42.353 ± 4.137 | 14.200 ± 0.818 |

Figure 4A:
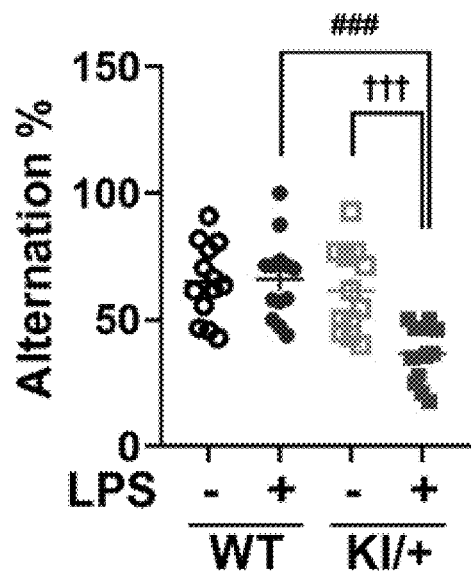
FIG. 4A to FIG. 4D show that intraperitoneal injection of LPS at a low concentration induces memory deficit in the Psen2 N141I mutation Alzheimer's disease mouse models.
Figure 4B:
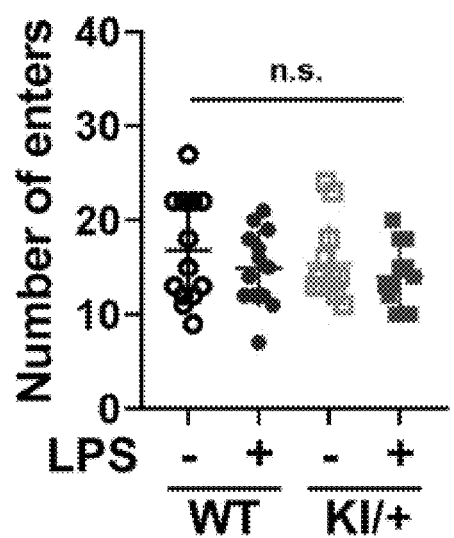

In Table 4, data for percentages of alternation and numbers of arm entries of each group in Y-maze are summarized (mean±SEM). As shown in FIGS. 4a and 4b, the arm alternation in the Y-maze exhibited no difference in memory ability between the wild-type mice of group 1 (13 mice) and the wild-type mice of group 2 with LPS injection (13 mice) in proportion to the secretion of inflammatory cytokines. The wild-type mice of group 1 without LPS injection did not differ in memory even from the Psen2 mutation Alzheimer's disease mice (12 mice) of group 3, which were not injected with LPS, but the memory was significantly decreased in the LPS-injected Psen2 mutation Alzheimer's disease mice (15 mice) of group 4. The total number of arm entries was similar across all the groups, indicating normal locomotor function.

4-2. T-Maze Assay

To further examine learning memory, a T-maze test with a food reward was conducted 20 hours after LPS injection. Groups 2 and 4 were injected with LPS at the concentration (0.35 μg/kg) that does not induce an inflammatory response in wild-type mice.

Figure 4C:
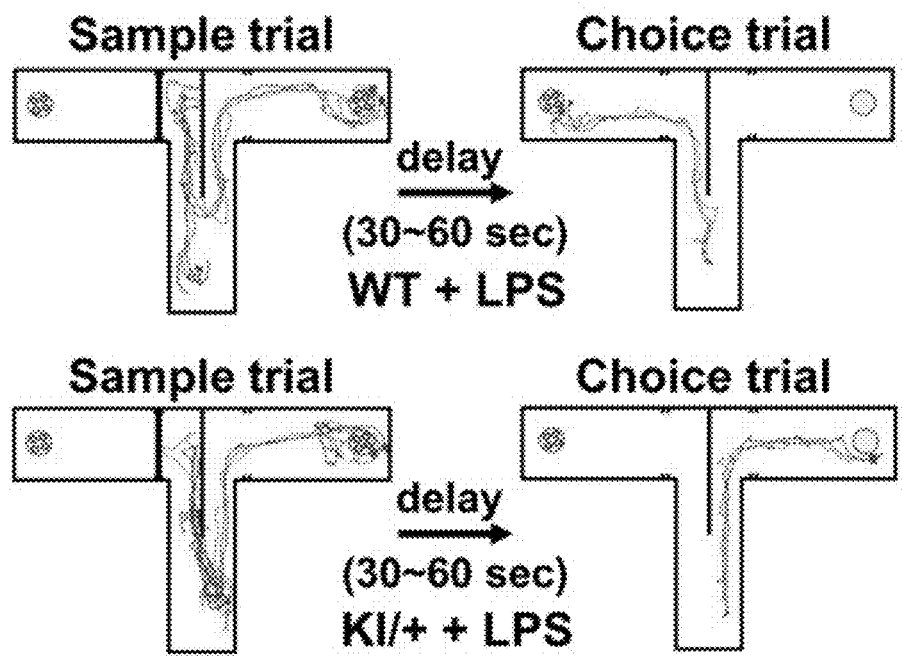

Specifically, T-maze was used to evaluate spatial learning and memory with reward alternation. As shown in FIG. 4C, the assay was conducted in white plastic arms of a T-shaped maze. Mice were acclimated to the maze and food reward for 5 min before the test. Then, in the test run, one arm was blocked and rewards were placed in another arm, and. Mice were placed at the base and ran to open arms to eat the reward. At the next trial, the previously closed arm was opened. Mice were placed back again at the base and chose one arm. If mice chose the newly opened arm, they were able to eat the reward. If mice incorrectly chose the previously visited arm, they did not get any rewards. The number of trials in which the correct arm was visited was expressed as a percentage of total arm entries.

TABLE 5

| T-maze | Success rate (%) |
| --- | --- |
| Group 1- WT(LPS(−)) | 68.831 ± 5.030 |
| Group 2- WT(LPS(+)) | 63.636 ± 3.907 |
| Group 3- KI/+(LPS(−)) | 64.113 ± 7.608 |
| Group 4- KI/+(LPS(+)) | 25.000 ± 3.761 |

Figure 4D:
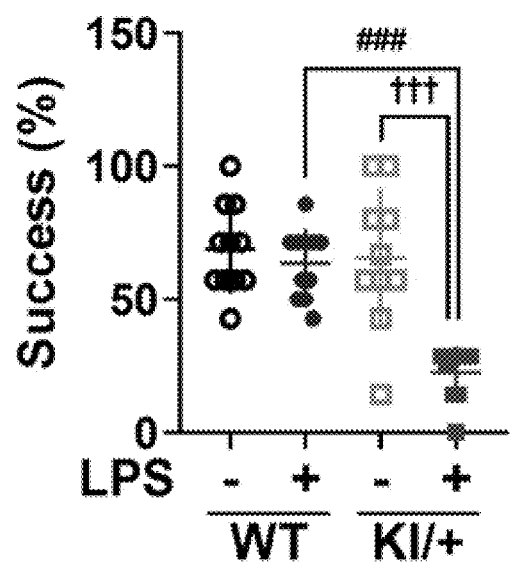

Data in Table 5 are mean±SEM of the success rates of T-maze in each group. As shown in FIG. 4D, there is no difference in learning and memory ability between the wild-type mice of group 1 (11 mice) and the LPS-injected wild-type mice of group 2 (11 mice) in proportion to the secretion of inflammatory cytokines. The wild-type mice of group 1 without LPS injection did not differ in learning and memory ability even from the Alzheimer's disease mice (10 mice) of group 3, which were not injected with LPS, but the LPS-injected Alzheimer's disease mice (10 mice) of group 4 significantly decreased in learning and memory.

From the data, it was understood that a low concentration of LPS induced a hyperactive immune response and caused memory deficit through the overproduction of inflammatory cytokines comprising IL-6 in Psen2 N141I KI/+ Alzheimer's disease mice, while the same concentration of LPS was innocuous to wild-type mice.

Example 5. Assay for Cytotoxicity of Didanosine

5-1. Preparation of Wild-Type Mouse-Derived Microglia

The brains were excised from 1- to 3-day-old neonatal mice and primary microglia were obtained from the brains and cultured in Dulbecco's modified Eagle's medium (DMEM, Corning) supplemented with 10% heat-inactivated fetal bovine serum (HI-FBS, Hyclone) and 1% penicillin-streptomycin (Hyclone). Primary microglia were isolated in vitro at day 12 by tapping. Purity of primary microglia was estimated by immunostaining with an antibody against IBA-1, which is a specific microglial marker.

5-2. Cytotoxicity Assay

To assay cytotoxicity of didanosine, microglia from wild-type (WT) mice were treated with 1, 5, or 10 μM of didanosine and measured for cell death rate. For use in this experiment, didanosine (CCL-D1-000017-G06) was provided from the Korea Chemical Bank.

Specifically, the microglia prepared in Example 5-1 were seeded at a density of $5 \times 10^4$ cells into 96-well plates. Next day, the seeded cells were incubated with 0, 1, 5, or 10 μM of didanosine for 12 hours and then co-stained with Hoechst 33342 (Invitrogen, H3570) and propidium iodide (PI; Sigma-Aldrich, P4170) for cell death measurement. Images of stained cells were captured using a fluorescence microscope (Axiovert 40 CFL; Carl Zeiss). Hoechst-positive and PI-positive cells were counted using NIH ImageJ software. Cell death rates were calculated by (number of PI-positive [dead] cells/number of Hoechst-positive [total] cells)×100.

Figure 5:
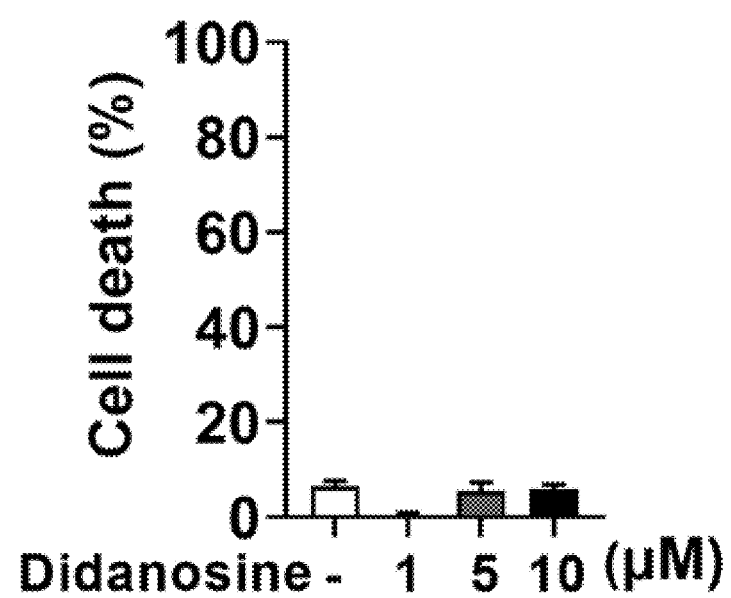
FIG. 5 shows cell death rates of microglia derived from wild-type mice after treatment with didanosine.

As can be seen in FIG. 5 and Table 6, didanosine was observed to have no cytotoxicity to cells.

TABLE 6

| Didanosine dose (μM) | Cell death rate (%) |
|---|---|
| 0 | 5.784 ± 0.985 |
| 1 | 2.026 ± 0.769 |
| 5 | 5.567 ± 1.694 |
| 10 | 5.847 ± 1.059 |

Example 6. Neuroinflammation Inhibitory Effect of Drug Using Microglia of Disease Animal Brains were excised from 1- to 3-day-old neonatal Psen2 N141I KI/+ mice and wild-type mice prepared in Example 1. Primary microglia derived from the wild-type and the Psen2 N141I KI/+ mice were cultured according to Example 5-1.

The prepared microglia were pretreated with 0, 5, or 10 μM of didanosine for 30 minutes and further with 1 LPS derived from *Escherichia coli* O111:B4(L4391). After 12 hours of incubation, the cytokine IL-6 released into the cell medium was quantitatively analyzed by ELISA. An ELISA kit for murine IL-6 was purchased from R&D system and used to measure a level of the cytokine in a culture medium according to the manufacturer's instructions.

Specifically, the primary microglia treated with didanosine were divided as follows.

TABLE 7

| Test Group | IL-6 (pg/mL) |
|---|---|
| Group 5- WT (LPS(didanosine 0 uM)) | 3424.373 ± 86.045 |
| Group 6- WT (LPS(didanosine 5 uM)) | 3099.967 ± 67.852 |
| Group 7- WT (LPS(didanosine 10 uM)) | 3009.218 ± 196.428 |
| Group 8- KI/+(LPS(didanosme 0 uM)) | 4730.879 ± 231.776 |
| Group 9- KI/+(LPS(didanosme 5 uM)) | 3749.965 ± 35.714 |
| Group 10- KI/+(LPS(didanosme 10 uM)) | 3261.407 ± 156.334 |

Figure 6:
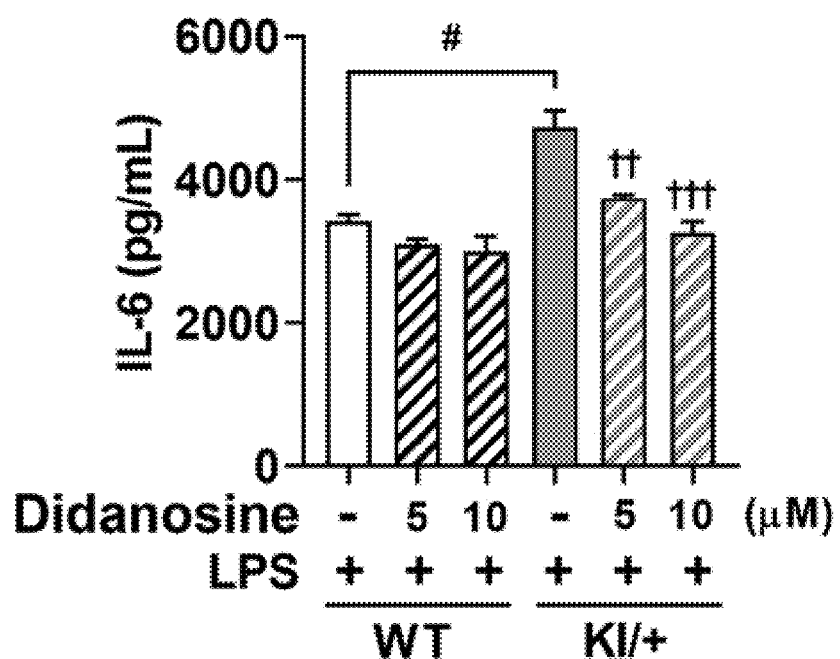
FIG. 6 shows secretion levels of the inflammatory cytokine IL-6 in microglia derived from wild-type (WT) and Psen2 N141I KI/+ Alzheimer's disease mice (KI/+) in response to LPS and didanosine.

As shown in Table 7 and FIG. 6, didanosine significantly decreased the elevated secretion level of IL-6 in LPS-treated microglia derived from Psen2 N141I KI/+ mice.

Example 7. Recovery Effect of Ability to Degrade Amyloid Beta Decreased by Psen2 N141I Mutation in Microglia According to Treatment of Didanosine Brains were excised from 1- to 3-day-old neonatal Psen2 N141I KI/+ mice and wild-type mice prepared in Example 1. Primary microglia derived from the wild-type and the Psen2 N141I KI/+ mice were cultured according to Example 5-1 and then seeded into 24-well plates covered with a cover glass.

Specifically, FITC signal-conjugated amyloid beta$_{1-42}$ was prepared with reference to the document (Cho, M.-H. et al. "Autophagy in microglia degrades extracellular β-amyloid fibrils and regulates the NLRP3 inflammasome." Autophagy 10, 1761-1775 (2014)).

FITC-conjugated amyloid beta oligomers were fibrilized for 24 hours in a medium.

The microglia were pretreated with 10 μM didanosine for 30 minutes, and then the fibrilized amyloid beta$_{1-42}$ (fAβ42) prepared above was directly applied at a concentration of 4 μM to the microglial cell culture. After 2 hours of incubation with the fibrilized amyloid beta, amyloid beta which was not engulfed but remained in the medium was removed through washing process.

Subsequently, the cells were continuously treated with didanosine for 24 hours, followed by fixation. The fixed cells were mounted on a slide glass and quantitatively measured for fibrilized amyloid beta remaining within the cells to compare degradation performance. Amyloid beta was quantitated by obtaining images taken by a confocal laser scanning microscope (LSM700) at intervals of 2 μm along the entire Z-axis of a randomly selected field and calculating pixel numbers of the HIC-labeled amyloid beta signals through ZEN (black edition; Carl Zeiss) software to measure relative fluorescent intensities.

Figure 7:
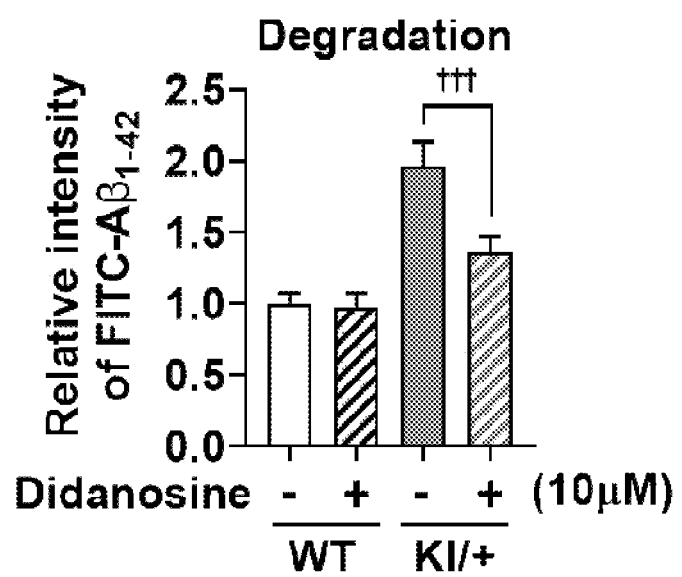
FIG. 7 is a view illustrating that didanosine recovers the ability to degrade amyloid beta from a decreased level in microglia derived from Psen2 N141I KI/+ mice (KI/+), which are Alzheimer's disease animal models, in comparison with wild-type (WT) mice.

As can be seen in FIG. 7 and Table 8, didanosine exhibited a therapeutic effect on a neuroinflammatory disease, e.g., Alzheimer's disease through recovery from the decreased amyloid beta degradation performance in Psen2 N141I KI microglia.

TABLE 8

| Test Group | Relative residual amyloid beta |
|---|---|
| Group 11- WT (didanosine 0 uM) | 1.000 ± 0.075 |
| Group 12- WT (didanosine 10 uM) | 0.973 ± 0.100 |
| Group 13- KI/+(didanosine 0 uM) | 1.964 ± 0.169 |
| Group 14- KI/+(didanosine 10 uM) | 1.353 ± 0.115 |

Example 8. Assay for Cytokine Expression in Psen2 N141I KI Model Mouse (KI/+)

Didanosine was intraperitoneally injected at a concentration of 5 mg/kg into wild-type mice (WT) and the Alzheimer's disease Psen2 N141I KI model mice (KI/+) constructed in Example 1, and after 4 hours, intraperitoneal injection of LPS at a concentration of 0.35 µg/kg was conducted.

Figure 8:
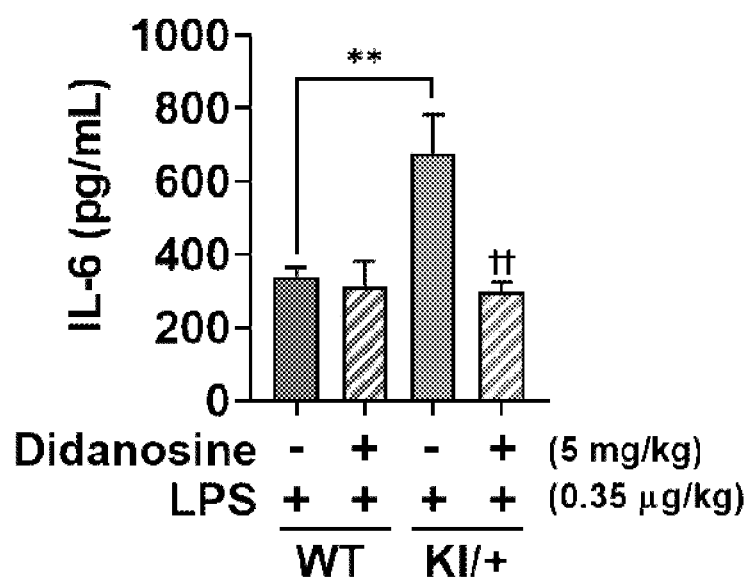
FIG. 8 is a view illustrating that the neuroinflammation-induced overexpression of IL-6 in wild-type (WT) and Psen2 N141I KI/+ mice (KI/+), which are Alzheimer's disease animal models, is remarkably suppressed by didanosine.

As shown in FIG. 8, a concentration of 0.35 µg/kg of LPS did neither induce any inflammatory response, nor increased blood IL-6 levels in wild-type mice, but induced neuroinflammation in the Psen2 N141I KI/+ mice, overproducing IL-6. In addition, the concentration of 5 mg/kg of didanosine corresponds to 0.4 mg/kg for humans (24 mg/60 kg), which is about 0.1 times or lower compared to the daily dose of 250 mg prescribed for HIV treatment.

Twenty-four hours after injection of didanosine, blood samples were taken from the mice, and sera were isolated therefrom and quantitatively analyzed for the cytokine IL-6 through ELISA. As shown in FIG. 8 and Table 9, didanosine remarkably reduce the level of IL-6 oversecreted by neuroinflammation

TABLE 9

| Test group | IL-6 (pg/mL) |
|---|---|
| Group 15- WT (LPS(didanosine 0 mg/kg)) | 339.507 ± 24.022 |
| Group 16- WT (LPS(didanosine 5 mg/kg)) | 312.679 ± 68.423 |
| Group 17- KI/+(LPS(didanosine 0 mg/kg)) | 675.229 ± 105.941 |
| Group 18- KI/+(LPS(didanosine 5 mg/kg)) | 297.484 ± 25.155 |

Example 9. Assay for Locomotor Activity and Memory in Psen2 N141I KI Model Mouse (KI/+)

Figure 9A:
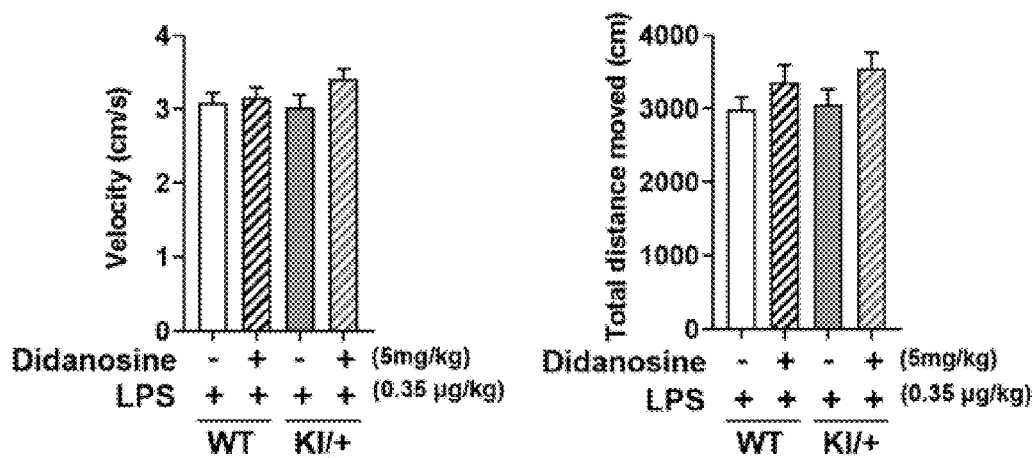
FIG. 9A shows that the administration of didanosine does not affect locomotor activity.
Figure 9B:
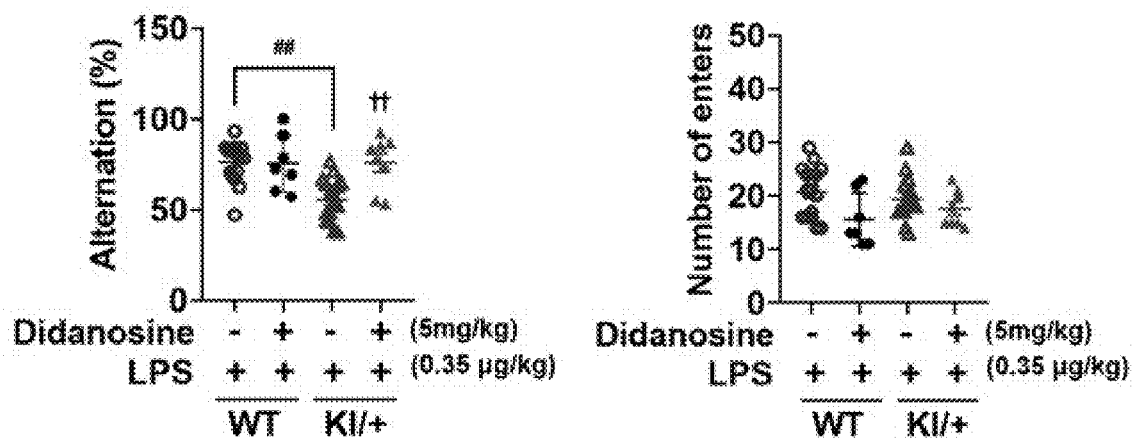
FIG. 9B shows that didanosine has an effect of recovering memory performance from a declined state.

Animal tests were performed using animal models of Psen2 N141I KI/+ disease. Didanosine was administered in the same manner as in Example 5 to wild-type mice and Psen2 N141I KI model mice (KI/+) constructed in Example 1, and after 4 hours, intraperitoneal injection of LPS at a concentration of 0.35 µg/kg was conducted thereon. As shown in FIG. 9B and Table 11, the concentration of 0.35 µg/kg of LPS corresponds to a very low concentration that does not induce memory deficit in wild-type mice, but induced neuroinflammation in Psen2 N141I KI/+ mice which thus underwent memory deficit.

For locomotor activity assay, an open field test was performed to measure locomotion speeds and total locomotor distance 24 hours after injection of didanosine. As shown in FIG. 9A and Table 10, intraperitoneal injection of didanosine did not affect locomotor activity.

TABLE 10

| Open field test | Locomotion speed (cm/s) | Total locomotor distance (cm) |
|---|---|---|
| Group 19- WT (LPS(didanosine 0 mg/kg)) | 3.09 ± 0.136 | 2983.939 ± 172.749 |
| Group 20- WT (LPS(didanosine 5 mg/kg)) | 3.155 ± 0.138 | 3354.104 ± 240.995 |
| Group 21- KI/+(LPS(didanosine 0 mg/kg)) | 3.019 ± 0.178 | 3050.195 ± 213.565 |
| Group 22- KI/+(LPS(didanosine 5 mg/kg)) | 3.410 ± 0.138 | 3549.364 ± 215.031 |

For memory recovery assay, spatial memory performance was assessed through Y-maze analysis 24 hours after didanosine injection. Specifically, a mouse was placed in one maze arm in a Y-maze and allowed to freely wander for 5 minutes. The Y-shaped arms were named A, B, and C, and whenever the mouse entered the arms, the names of the arms were recorded. The number of entries into new arms that the mice did not enter just before were calculated and analyzed as follows: Alternation (%)=(three consequent different trials (arm)/(total number of entry−2))×100. The total numbers of entries into the arms were same across the groups, indicating same locomotor activity thereamong.

As shown in FIG. 9B and Table 11, didanosine recovered the decreased memory performance of the Alzheimer's disease Psen2 N141I KI model mice to the memory level of wild-type mice. In detail, as confirmed in Example 4-1, the low concentration of LPS did neither cause memory decline, nor affect locomotor activity in the normal group. Thus, the LPS-injected normal group did not differ in memory and locomotor activity from the normal group without LPS injection. The low concentration of LPS caused memory deficit only in the Alzheimer's disease-induced groups. That is, didanosine recovered the decreased memory of the LPS-injected, Alzheimer's disease Psen2 N141I KI mice to the memory level of the wild-type mice without LPS injection.

TABLE 11

| Y- maze | Alternation percent | No. of Arm entry |
|---|---|---|
| Group 19- WT (LPS(didanosine 0 mg/kg)) | 76.261 ± 2.810 | 30.239 ± 4.694 |
| Group 20- WT (LPS(didanosine 5 mg/kg)) | 75.512 ± 5.919 | 34.707 ± 8.543 |
| Group 21- KI/+(LPS(didanosine 0 mg/kg)) | 55.485 ± 2.942 | 27.000 ± 4.481 |
| Group 22- KI/+(LPS(didanosine 5 mg/kg)) | 75.977 ± 5.160 | 30.545 ± 7.187 |

Example 10. Therapeutic Effect of Drug on Neuroinflammation in Microglial of Disease Animal Brains were excised from 1- to 3-day-old neonatal Psen2 N141I KI/+ mice and wild-type mice prepared in Example 1. Primary microglia derived from the wild-type and the Psen2 N141I KI/+ mice were cultured according to Example 5-1.

To observe the therapeutic effect of didanosine, the prepared microglia were pretreated with 1 µg/mL LPS and then 10 µM of didanosine was treated after 1 hour. After 11 hours of incubation, the cytokine IL-6 released into the cell medium was quantitatively analyzed by ELISA. An ELISA kit for murine IL-6 was purchased from R&D system and used to measure a level of the cytokine in a culture medium according to the manufacturer's instructions.

Figure 10:
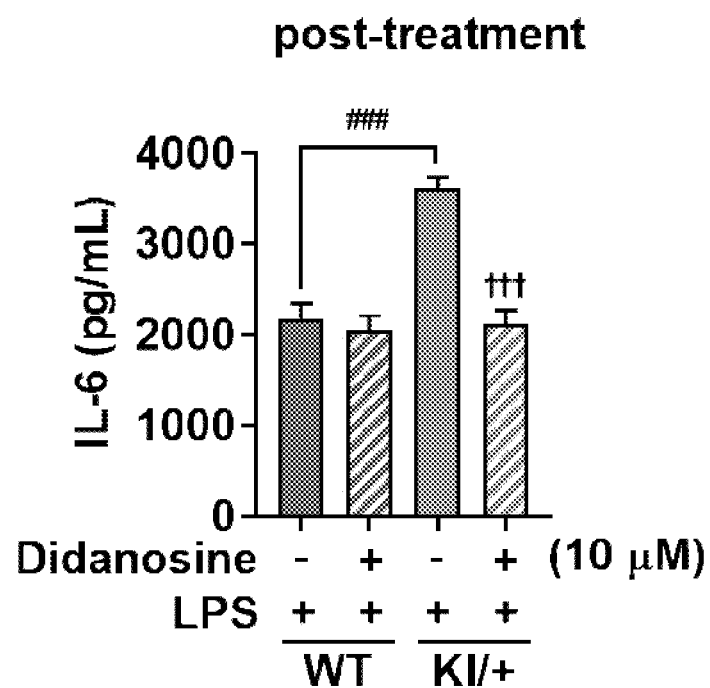
FIG. 10 shows that didanosine decreases an increased secretion level of IL-6 in microglia derived from Psen2 N141I KI/+ mice in which neuroinflammation has been induced by LPS.

The primary microglia treated with didanosine were divided as follows. As shown in FIG. 10 and Table 12, application of didanosine to the Psen2 N141I KI/+ mouse-derived microglial cells where LPS induced neuroinflammation significantly decreased the elevated secretion level of IL-6, demonstrating a therapeutic effect of didanosine on neuroinflammation.

TABLE 12

| Test group | IL-6 (pg/mL) |
|---|---|
| Group 23- WT (LPS(didanosine 0 uM)) | 2160 ± 176.635 |
| Group 24- WT (LPS(didanosine 10 uM)) | 2040 ± 164.317 |
| Group 25- KI/+(LPS(didanosme 0 uM)) | 3607.5 ± 128.087 |
| Group 26- KI/+(LPS(didanosine 10 uM)) | 2115 ± 151.959 |

Example 11. Assay for Locomotor Activity and Memory in 5×FAD Mouse Model

As an animal model for use in research into Alzheimer's disease, a 5×FAD mouse model that has a total of 5 AD-related mutant APP and PSEN1 genes (APP; Swedish (K670N/M671L), Florida (I716V), and London (V717I) mutations and PSEN1; M146L and L286V mutations) was employed in this assay. The APP and PSEN1 mutant genes are expressed under the control of Thy1 (mature neuron-specific label) promoter and cause severe amyloid pathology and behavior deficiency even in hemizygous mice (Jawhar S. et al. "*Motor deficits, neuron loss, and reduced anxiety coinciding with axonal degeneration and intraneuronal Aβ aggregation in the 5XFAD mouse model of Alzheimer's disease.*" Neurobiology of Aging 196. e29-40 (2012)).

Didanosine was intraperitoneally injected at a concentration of 0.5 mg/kg/day into 6-month-old 5×FAD mice and wild-type mice five days in series per week for a total of four weeks. The concentration of 0.5 mg/kg of didanosine corresponds to 0.04 mg/kg for humans (2.4 mg/60 kg), which is about 0.01 times or lower compared to the daily dose of 250 mg prescribed for HIV treatment.

Figure 11A:
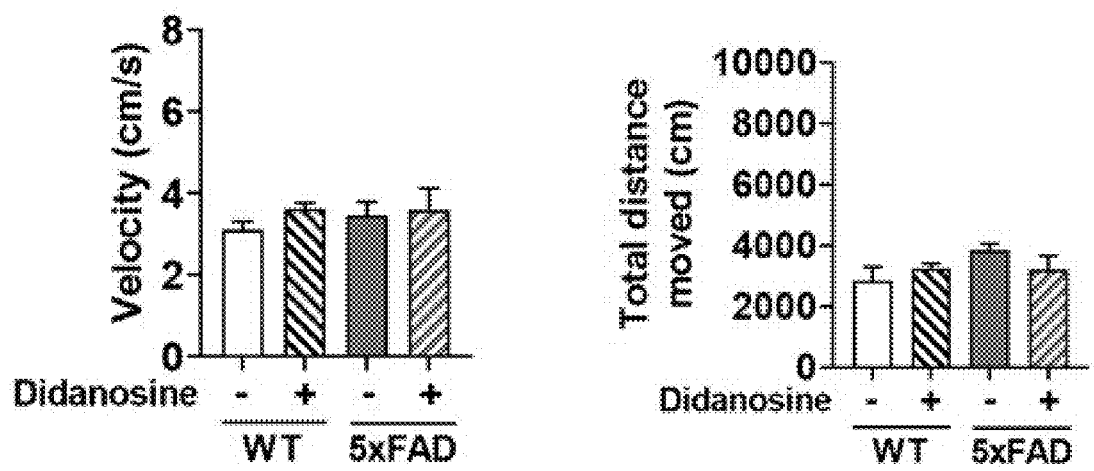
FIG. 11A shows that the administration of didanosine does not affect locomotor activity in wild-type mice and 5×FAD disease animal models.

For locomotor activity assay after injection of didanosine, an open field test was performed in the same manner as in Example 9 to measure locomotion speeds and total locomotor distance. As shown in FIG. 11A and Table 13, intraperitoneal injection of didanosine did not affect locomotor activity.

TABLE 13

| Open field test | Locomotion speed (cm/s) | Total locomotor distance (cm) |
|---|---|---|
| Group 27- WT (didanosine (0 mg/kg/day)) | 3.118 ± 0.197 | 2841.843 ± 445.852 |
| Group 28- WT (didanosine (0.5 mg/kg/day)) | 3.616 ± 0.154 | 3253.840 ± 138.739 |
| Group 29- 5xFAD (didanosine (0 mg/kg/day)) | 3.464 ± 0.335 | 3855.947 ± 187.071 |
| Group 30- 5xFAD (didanosine (0.5 mg/kg/day)) | 3.607 ± 0.525 | 3212.850 ± 438.732 |

Figure 11B:
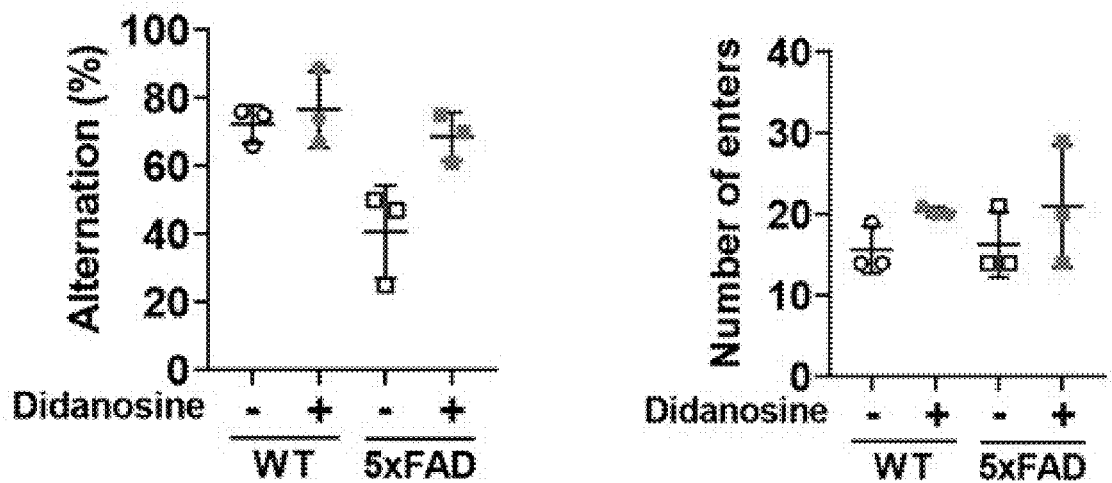
FIG. 11B shows that didanosine has an effect of recovering memory performance from a declined state in 5×FAD disease animal models.

For memory recovery assay, spatial memory performance was assessed in the same manner as in Example 9 after injection of didanosine. As shown in FIG. 11B and Table 14, didanosine was observed to make a recovery from the memory decline induced in the 5×FAD (6 month) Alzheimer's disease models.

TABLE 14

| Y- maze | Alternation percent | No. of Arm entry |
|---|---|---|
| Group 27- WT (didanosine (0 mg/kg/day)) | 72.333 ± 3.180 | 15.667 ± 1.667 |
| Group 28- WT (didanosine (0.5 mg/kg/day)) | 76.667 ± 6.489 | 20.333 ± 0.333 |
| Group 29- 5xFAD (didanosine (0 mg/kg/day)) | 40.667 ± 7.881 | 16.333 ± 2.333 |
| Group 30- 5xFAD (didanosine (0.5 mg/kg/day)) | 68.667 ± 4.096 | 21.000 ± 4.359 |

Example 12. Assay for Recovery from Neuroinflammation in 5×FAD Mouse Model

After completion of the experiment in Example 11, hippocampal tissues were isolated from the 5×FAD mouse and examined for expression of IL-6 gene (Il-6). Specifically, an expression level of Il-6 mRNA was measured using quantitative RT-PCR (qRT-PCR). In this regard, RNA was extracted from the isolated hippocampal tissues and used to synthesize cDNA with ImProm-II Reverse Transcriptase kit (Promega). PCR primers were commercially synthesized (Cosmo Genetech). qRT-PCR was carried out using murine cDNA-specific Taq Polymerase (Invitrogen) and the primers listed in Table 15. In CFX96 Real-Time System (Bio-Rad), 50-cycle amplification was applied to all the primers by using TOPreal™ qPCR 2×PreMIX (SYBR Green with low ROX) (Enzynomics). Actb was used as a reference gene for normalization.

TABLE 15

| Gene | Gene reference number | | 5'-primer sequence-3' |
|---|---|---|---|
| IL-6 | NM_031168.2 | F | CTGGATATAATCAGGAAATTTGC (SEQ ID NO: 3) |
| | | R | AAATCTTTTACCTCTTGGTTGA (SEQ ID NO: 4) |

Figure 12:
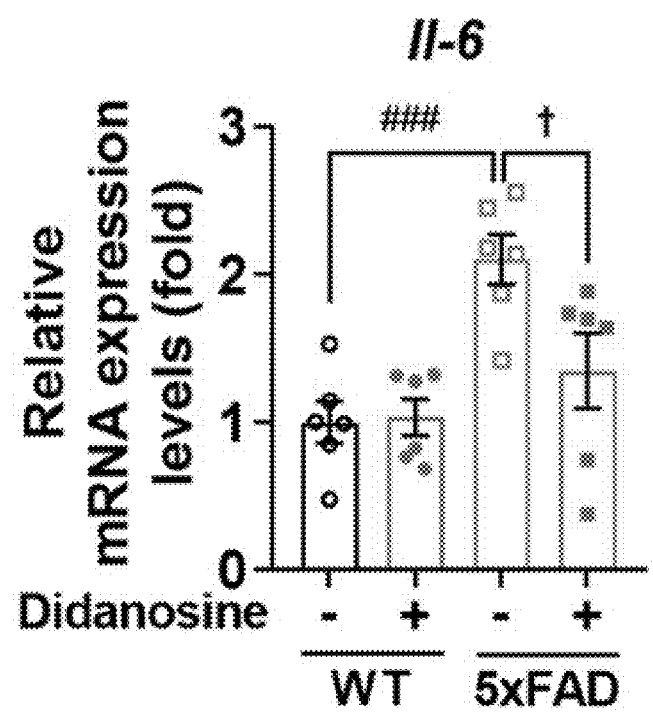
FIG. 12 shows that didanosine has a recovery effect on the brain from inflammation in 5×FAD disease animal models.

As shown in FIG. 12 and Table 16, the expression level of IL-6 which was elevated in the 5×FAD mouse brain tissues was lowered by didanosine, demonstrating that didanosine has a recovery effect from brain inflammation, specifically, hippocampal inflammation and thus a therapeutic effect on neuroinflammatory disease.

TABLE 16

| Test group | Il-6 mRNA expression (fold) |
|---|---|
| Group 27- WT (didanosine (0 mg/kg/day)) | 1.000 ± 0.141 |
| Group 28- WT (didanosine (0.5 mg/kg/day)) | 1.033 ± 0.124 |
| Group 29- 5xFAD (didanosine (0 mg/kg/day)) | 2.104 ± 0.169 |
| Group 30- 5xFAD (didanosine (0.5 mg/kg/day)) | 1.348 ± 0.255 |

Example 13. Statistical Analysis

Data in the Examples above were acquired in at least three independent experiments and are presented as mean±standard error of the mean values (SEM). Statistical analysis was performed by using Student's unpaired t-test, one-way ANOVA, or two-way ANOVA. Statistical significance was analyzed using GraphPad Prism.

Although the preferred embodiments of the present disclosure have been disclosed for illustrative purposes, those skilled in the art will understand that other specific variations and modifications are possible, without departing from the technical spirit or essential features of the present disclosure. Therefore, it should be understood that the Examples described above are illustrative in all respects and not limited.

The invention claimed is:

1. A method for preventing or treating a neuroinflammatory disease, comprising a step of administering didanosine or a pharmaceutically acceptable salt thereof to a subject in need thereof,
   wherein the subject has an increased level of an inflammatory cytokine in a central nervous system, and
   wherein the neuroinflammatory disease is a disease caused by neuroinflammation in the central nervous system, and is selected from the group consisting of multiple sclerosis, neuroblastoma, stroke, dementia, Alzheimer's disease, cognitive impairment, memory impairment, disturbance of attention, Parkinson's disease, Lou Gehrig's disease, Huntington's disease, Creutzfeldt Jakob disease, post-traumatic stress disorder, depression, schizophrenia, neuropathic pain, and amyotrophic lateral sclerosis.

2. The method of claim 1, wherein the subject has a decreased activity of microglia in degrading amyloid beta.

3. The method of claim 1, wherein the method inhibits expression of a neuroinflammatory cytokine in microglia.

4. The method of claim 1, wherein the method recovers microglial activity of amyloid beta degradation.

5. The method of claim 1, wherein the didanosine or a pharmaceutically acceptable salt thereof is administered at a daily dose of 0.001 to 4 mg/kg.

6. The method of claim 1, wherein the neuroinflammatory disease is hereditary dementia.

7. The method of claim 1, wherein the neuroinflammatory disease is familial Alzheimer's disease.

8. The method of claim 1, wherein the neuroinflammatory disease is an Alzheimer's disease or dementia related with Alzheimer's disease having at least a genetic mutation in at least one selected from the group consisting of amyloid precursor protein (APP), presenilin 1 (PSEN1), and presenilin 2 (PSEN2).

9. The method of claim 8, wherein the genetic mutation in the Presenilin 2 gene comprises at least one selected from the group consisting of PSEN N141, A85V, N141Y, M174I, G212V, A237V, M239I and M239V.

10. A method of promoting amyloid beta degradation in microglia, comprising a step of administering didanosine or a pharmaceutically acceptable salt thereof to a subject in need thereof,
    wherein the subject has a neuroinflammatory disease caused by an increased level of an inflammatory cytokine in a central nervous system.

11. The method of claim 10, wherein the microglia have at least a genetic mutation in at least one selected from the group consisting of amyloid precursor protein (APP), presenilin 1 (PSEN1), and presenilin 2 (PSEN2).

12. The method of claim 1, wherein the neuroinflammation is hippocampal tissue inflammation.

* * * * *

SEQUENCE LISTING

```
Sequence total quantity: 4
SEQ ID NO: 1              moltype = DNA  length = 1347
FEATURE                   Location/Qualifiers
misc_feature              1..1347
                          note = Psen2 N141I
source                    1..1347
                          mol_type = other DNA
                          organism = synthetic construct
SEQUENCE: 1
atgctcgcat tcatggcctc tgacagcgag gaagaggtgt gtgatgagcg acgtccttg    60
atgtcagccg agagccccac atctcgctcc tgccaggaag gcaggccagg cccggaggat   120
ggagagagca ctgcccagtg gaggactcag gagagcgaag aagactgtga agaggacccg   180
gaccgctacg catgcagtgg ggctcctggg cgaccgtcgg gcctggagga agagctgacc   240
ctcaagtatg gggcgaagca tgtgatcatg ctattcgtgc ctgtcacgct gtgtatgatc   300
gtggtggtgg ccactatcaa gtctgtgcgt ttctacactg agaagaacgg gcagctcatc   360
tacacgccct tcacggagga cacgccctcg gtgggccagc ggctcctcaa ctccgtgctt   420
atcaccctca tcatgatcag cgtcatcgta gtcatgacca tcttcctcgt ggtactctac   480
aagtatcgat gctacaagtt catccatggc tggctgatca tgtcctccct gatgctcctc   540
ttcttgttca cctacatcta cctcggggaa gtgctcaaga cctacaatgt ggccatggac   600
tatcccacac tcttcctggc tgtctggaac ttcggggcag tgggcatggt gtgcatccac   660
tggaaggggc ctctggtgct gcagcaggct taccttattg tgatcagcgc actcatggcc   720
ctggtgttca tcaagtacct gccggagtgg tctgcctggg tcatcttggg tgccatctct   780
gtgtacgatc tcgtggccgt gctgtgcccc aaagggccac tgaggatgct ggtggaaact   840
gcccaggaga gaaatgagcc catatttcct gccctgatat actcatctgc catggtgtgg   900
acggtgggca tggcaaagct ggacccctcc tctcaaggag cgctgcagct ccctatgac    960
ccagagatgg aagaagactc ctacgacagt ttgagaaac cctcatacc tgaagccttc    1020
gaagcccccc tgcctggcta cccaggggag gagctggagg aggaggagga aagggcgtg    1080
aagctcggcc tgggagactt catcttctac agcgtcctgg tgggcaaggc tgcagccact   1140
ggcaacggag actggaacac tacgctggcc tgtttatcg ccatcctcat ggcttgtgt    1200
ctcaccctcc tgctgcttgc tgtgttcaag aaggctctgc ccgccctccc catctccatc   1260
acctttggac tcatcttcta cttctccaca gacaacctgg tgcgccttt catggacact    1320
ctggcctccc accagctcta catctga                                       1347

SEQ ID NO: 2              moltype = DNA  length = 1347
FEATURE                   Location/Qualifiers
misc_feature              1..1347
                          note = Psen2 wild type
source                    1..1347
                          mol_type = other DNA
                          organism = synthetic construct
SEQUENCE: 2
atgctcgcat tcatggcctc tgacagcgag gaagaggtgt gtgatgagcg acgtccttg    60
atgtcagccg agagccccac atctcgctcc tgccaggaag gcaggccagg cccggaggat   120
ggagagagca ctgcccagtg gaggactcag gagagcgaag aagactgtga agaggacccg   180
gaccgctacg catgcagtgg ggctcctggg cgaccgtcgg gcctggagga agagctgacc   240
ctcaagtatg gggcgaagca tgtgatcatg ctattcgtgc ctgtcacgct gtgtatgatc   300
gtggtggtgg ccactatcaa gtctgtgcgt ttctacactg agaagaacgg gcagctcatc   360
tacacgccct tcacggagga cacgccctcg gtgggccagc ggctcctcaa ctccgtgctt   420
atcaccctca tcatgatcag cgtcatcgta gtcatgacca tcttcctcgt ggtactctac   480
aagtatcgat gctacaagtt catccatggc tggctgatca tgtcctccct gatgctcctc   540
ttcttgttca cctacatcta cctcggggaa gtgctcaaga cctacaatgt ggccatggac   600
tatcccacac tcttcctggc tgtctggaac ttcggggcag tgggcatggt gtgcatccac   660
tggaaggggc ctctggtgct gcagcaggct taccttattg tgatcagcgc actcatggcc   720
ctggtgttca tcaagtacct gccggagtgg tctgcctggg tcatcttggg tgccatctct   780
gtgtacgatc tcgtggccgt gctgtgcccc aaagggccac tgaggatgct ggtggaaact   840
gcccaggaga gaaatgagcc catatttcct gccctgatat actcatctgc catggtgtgg   900
acggtgggca tggcaaagct ggacccctcc tctcaaggag cgctgcagct ccctatgac    960
ccagagatgg aagaagactc ctacgacagt ttgagaaac cctcatacc tgaagccttc    1020
gaagcccccc tgcctggcta cccaggggag gagctggagg aggaggagga aagggcgtg    1080
aagctcggcc tgggagactt catcttctac agcgtcctgg tgggcaaggc tgcagccact   1140
ggcaacggag actggaacac tacgctggcc tgtttatcg ccatcctcat ggcttgtgt    1200
ctcaccctcc tgctgcttgc tgtgttcaag aaggctctgc ccgccctccc catctccatc   1260
acctttggac tcatcttcta cttctccaca gacaacctgg tgcgccttt catggacact    1320
ctggcctccc accagctcta catctga                                       1347

SEQ ID NO: 3              moltype = DNA  length = 23
FEATURE                   Location/Qualifiers
misc_feature              1..23
                          note = Primer(F) for IL-6
source                    1..23
                          mol_type = other DNA
                          organism = synthetic construct
SEQUENCE: 3
ctggatataa tcaggaaatt tgc                                           23

SEQ ID NO: 4              moltype = DNA  length = 22
FEATURE                   Location/Qualifiers
misc_feature              1..22
```

```
                   note = Primer(R) for IL-6
source             1..22
                   mol_type = other DNA
                   organism = synthetic construct
SEQUENCE: 4
aaatcttta cctcttggtt ga                                    22
```